(12) United States Patent  (10) Patent No.: US 8,743,200 B2
    Anderson                       (45) Date of Patent:       Jun. 3, 2014

(54) ACTIVITY MONITOR

(71) Applicant: Charles William Anderson, Boulder, CO (US)

(72) Inventor: Charles William Anderson, Boulder, CO (US)

(73) Assignee: HiPass Design LLC, Boulder, CO (US)

( * ) Notice: Subject to any disclaimer, the term of this patent is extended or adjusted under 35 U.S.C. 154(b) by 0 days.

(21) Appl. No.: 13/718,623

(22) Filed: Dec. 18, 2012

(65) Prior Publication Data

US 2013/0182107 A1    Jul. 18, 2013

Related U.S. Application Data

(60) Provisional application No. 61/587,102, filed on Jan. 16, 2012.

(51) Int. Cl.
    *H04N 7/18*       (2006.01)
    *G06K 9/00*       (2006.01)

(52) U.S. Cl.
    CPC .......... *G06K 9/00624* (2013.01); *H04N 7/183* (2013.01)
    USPC .......................................................... 348/143

(58) Field of Classification Search
    CPC ............................ H04N 7/18; G06K 9/00624
    USPC .......................................................... 348/143
    See application file for complete search history.

(56) References Cited

U.S. PATENT DOCUMENTS

| | | | |
|---|---|---|---|
| 4,793,010 A * | 12/1988 | Gross et al. | 5/109 |
| 4,856,130 A * | 8/1989 | Berkovich | 5/109 |
| 5,684,460 A * | 11/1997 | Scanlon | 340/573.1 |
| 6,315,740 B1 | 11/2001 | Singh | |
| 6,544,200 B1 * | 4/2003 | Smith et al. | 600/595 |
| 7,557,718 B2 * | 7/2009 | Petrosenko et al. | 340/573.1 |
| 8,109,891 B2 | 2/2012 | Kramer et al. | |
| 8,296,686 B1 * | 10/2012 | Tedesco et al. | 715/865 |
| 2003/0025599 A1 * | 2/2003 | Monroe | 340/531 |
| 2003/0231778 A1 * | 12/2003 | Landa | 381/77 |
| 2004/0190767 A1 * | 9/2004 | Tedesco et al. | 382/156 |
| 2006/0206379 A1 * | 9/2006 | Rosenberg | 705/14 |

(Continued)

FOREIGN PATENT DOCUMENTS

WO        02082999 A1    10/2002

OTHER PUBLICATIONS

BioLert Ltd., Electro Medical Systems, Epilert Epilepsy Seizures Alert, www.Biolertsys.com, retrieved on Oct. 29, 2012.

*Primary Examiner* — Jeremaiah C Hallenbeck-Huber
(74) *Attorney, Agent, or Firm* — Holland & Hart LLP

(57) ABSTRACT

An activity monitor system monitors a location using a sensor system and detects and responds to "interesting events." The system may detect events based on video processing of a substantially live sequence of images from a video camera. The system may use multi-region processing including modifying event detection based on motion in one or more regions, motion transitions, and/or motion entry and/or exit points. Events may be detected based on other sensors and the system may use a combination of sensor data to detect events. The system may store event data from the one or more sensors (e.g., video, audio, etc.) for interesting events and/or trigger alarm actions. Alarm actions may include sounding an audible alarm and enabling a substantially live video display on a monitoring device concurrently with the audible alarm. In embodiments, the activity monitor system is implemented using a smartphone and a wireless network camera.

26 Claims, 23 Drawing Sheets

(56) References Cited

U.S. PATENT DOCUMENTS

2006/0220884 A1* 10/2006 Thompson .................. 340/573.1
2008/0021731 A1* 1/2008 Rodgers ............................ 705/2
2010/0198094 A1* 8/2010 Turicchia et al. ............. 600/528
2011/0087079 A1* 4/2011 Aarts ............................ 600/300
2011/0305376 A1* 12/2011 Neff ............................... 382/128
2012/0026308 A1* 2/2012 Johnson et al. ................. 348/77
2012/0108999 A1* 5/2012 Leininger et al. ............. 600/546
2012/0140068 A1* 6/2012 Monroe et al. ................ 348/143

* cited by examiner

ACTIVITY MONITOR

CROSS REFERENCES

This application claims the benefit of U.S. Provisional Application No. 61/587,102, entitled "Activity Monitor," filed on Jan. 16, 2012, the disclosure of which is expressly incorporated by reference in its entirety for all purposes.

BACKGROUND

1. Field

The present invention is in the technical field of activity monitoring and alarm processing. More particularly, the present invention is in the technical field of monitoring and recording activities of a patient and performing actions based on the observed activities.

2. Relevant Background

It is useful to be able to remotely monitor one or more locations and trigger a response such as an alarm under certain conditions, for example movement or sound. Examples of this are monitoring a baby in its crib for crying, a pool for someone falling in, or a person with epilepsy for a seizure. Typically this is now done with some sort of sensor, examples include an intercom for sound, an infra-red sensor for movement, or a video camera. These devices require continuous monitoring by a person who is deciding whether a response of some sort is required.

While some automated systems exist for triggering a response in real-time (i.e., triggering an alarm as the action is occurring), these systems typically rely on motion sensors attached to the patient or to a specific apparatus (e.g., bed, etc.). These systems may be difficult to set up and calibrate for different patients, monitored pathologies and/or monitored locations.

SUMMARY

An activity monitor system that detects "interesting events" based on data from a sensor system and performs actions based on detecting the events is described. The activity monitor system may detect interesting events based on video processing of a substantially live sequence of images from a video camera. The activity monitor system may detect events based on other sensors and may use a combination of sensor data to detect events. The activity monitor system may store event data from the one or more sensors (e.g., video, audio, etc.) for interesting events and/or trigger an alarm action. Alarm actions may include sounding an audible alarm and enabling a substantially live video display on a monitoring device concurrently with the audible alarm.

The activity monitor system may use video processing techniques such as motion estimation and multi-region processing to detect events. Event detection may include integrating motion levels from one or more regions to determine a motion alert level. Comparing the motion alert level with one or more thresholds may trigger various actions such as recording the event and/or performing an alarm action. Multi-region processing may include suppressing event detection and/or alarm generation based on motion in one or more regions, motion transitions, and/or motion entry and/or exit points. The activity monitor system may use other sensor information such as an audio signal to detect events. The activity monitor system may include a user interface to allow customization of event detection and/or behavior upon detecting events. In embodiments, the activity monitor system is implemented using a smartphone and a wireless network camera (e.g., webcam, etc.).

Some embodiments are directed to a system for monitoring a patient that includes a video camera that captures images of a patient location and a video processing device coupled with the video camera. In embodiments, the video processing device is configured to receive a substantially live sequence of the captured images, compare each image of the sequence of images with one or more preceding images to determine motion levels associated with each of the sequence of images, determine a motion alert level signal based at least in part on an integration function of the motion levels, compare the motion alert level signal with a motion alarm threshold, and generate a motion alarm signal based at least in part on determining that the motion alert level signal exceeds the motion alarm threshold. The system may include a video display device coupled with the video camera and an alarm processor coupled with the motion alarm signal, where the alarm processor may be configured to trigger an audible alarm based at least in part on the motion alarm signal and enable, concurrently with the audible alarm, a substantially live display of the sequence of images on the video display device.

In embodiments, the system includes a microphone that captures an audio signal from the patient location and an audio detector coupled with the microphone. The audio detector may be configured to determine an audio meter signal based at least in part on the received audio signal, determine an audio level signal based at least in part on an integrating function of a plurality of values of the audio meter signal, compare the audio level signal with an audio alarm threshold, and generate an audio alarm signal responsive to detecting that the audio level signal exceeds the audio alarm threshold. Determining the audio level signal may include comparing the plurality of values of the audio meter signal to a high audio threshold, increasing the audio level signal based on values of the audio meter signal that exceed the high audio threshold, and decreasing the audio level signal based on values of the audio meter signal that do not exceed the high audio threshold. The audio alert integrator may be further configured to compare the plurality of audio values of the audio meter signal to a low audio threshold to produce a low audio detection signal, determine a low audio level signal based at least in part on the low audio detection signal, compare the low audio level signal with a low audio alarm threshold, and generate a low audio alarm signal responsive to detecting that the low audio level signal exceeds the low audio alarm threshold. The system may include an alarm processor coupled with the motion alarm signal and the audio alarm signal. The alarm processor may be configured to trigger an alarm action based on one or more of the motion alarm signal and the audio alarm signal.

Embodiments are directed to a method for monitoring a patient. The method may include receiving a substantially live sequence of images of a patient location, comparing each image of the sequence of images with one or more preceding images to determine motion levels associated with the image, determining a motion alert level signal based at least in part on an integrating function of the motion levels, comparing the motion alert level signal with a motion alarm threshold, and generating a motion alarm signal based at least in part on detecting that the motion alert level signal exceeds the motion alarm threshold. The method may include triggering an audible alarm at a monitoring device based on the motion alarm signal and enabling a substantially live display of the sequence of images on a display device of the monitoring device concurrently with the audible alarm. The method may include initiating bidirectional audio communication between the patient and a monitoring device based on the motion alarm signal.

In embodiments, comparing each image of the sequence of images with one or more preceding images includes comparing a first region of each image of the sequence of images with the first region of the one or more preceding images to generate a first motion level associated with the first region for each of the sequence of images, comparing the first motion level to a first threshold to generate a first motion detection signal associated with the first region, comparing a second region of each image of the sequence of images with the second region of the one or more preceding images to generate a second motion level associated with the second region for each of the sequence of images, and comparing the second motion level to the first threshold to produce a second motion detection signal associated with the second region. Determining the motion alert level signal may include applying a first weighting coefficient to the first motion detection signal, applying a second weighting coefficient to the second motion detection signal, and determining the motion alert level signal based at least in part on the weighted first motion detection signal and the weighted second motion detection signal. The method may include determining, for a motion event of the patient based on the comparing of the first and second regions, a region transition from the first region to the second region and suppressing triggering of alarm actions based on the motion alarm signal for a predetermined time period based on the region transition for the motion event. The first region may be a center region and the second region may be an edge region.

The regions may be user-definable. For example, the method may include receiving user input identifying a first portion of a display screen and determining one of the first region or the second region based at least in part on the received user input. Receiving user input may include enabling a substantially live display of the sequence of images on the display device and receiving user input corresponding to a selection of the first portion of the display screen.

The method may include comparing the motion level signal with a motion event threshold and storing, responsive to the motion level signal exceeding the motion event threshold, a time period of the sequence of images. The time period may be based at least in part on an elapsed time of the motion level signal exceeding the motion event threshold. Storing the time period of the sequence of images may include storing a predetermined time period of the sequence of images received prior to the motion level signal exceeding the motion event threshold. The method may include associating a value of the motion level signal for each stored subset of the sequence of images and displaying a stored event list, wherein each stored event of the stored event list comprises a stored time period of the sequence of images and the associated motion level signal value.

In embodiments, determining the motion level signal based on the motion detection signal includes comparing the motion detection signal to a motion threshold, increasing the motion level signal responsive to determining that the motion detection signal exceeds the motion threshold, and decreasing the motion level signal responsive to determining that the motion detection signal is less than the motion threshold. In embodiments, an increase step value of the motion level signal is greater than a decrease step value of the motion level signal.

Some embodiments are directed to a computer program product for monitoring a patient. The computer program product includes a non-transitory computer-readable medium that includes code for causing a computer to receive a substantially live sequence of images of a patient location, compare each image of the sequence of images with one or more preceding images to determine a motion level associated with the image, determine a motion alert level signal based at least in part on an integrating function of the motion levels of the sequence of images, compare the motion alert level signal with a motion alarm threshold, and generate a motion alarm signal responsive to detecting that the motion level signal exceeds the motion alarm threshold. The computer-readable medium may include code for causing the computer to trigger an audible alarm at a monitoring device responsive to the motion alarm signal, and enable, concurrently with the audible alarm, a substantially live display of the sequence of images on a display device of the monitoring device.

In embodiments, the code for causing the computer to compare each image of the sequence of images with the one or more preceding images includes code for causing the computer to compare a first region of each image of the sequence of images with the first region of the one or more preceding images to generate a first motion level associated with the first region for each of the sequence of images, compare the first motion level to a first threshold to generate a first motion detection signal associated with the first region, compare a second region of each image of the sequence of images with the second region of the one or more preceding images to generate a second motion level associated with the second region for each of the sequence of images, and compare the second motion level to the first threshold to produce a second motion detection signal associated with the second region.

In embodiments, the computer-readable medium includes code for causing the computer to apply a first weighting coefficient to the first motion detection signal, apply a second weighting coefficient to the second motion detection signal, and determine the motion alert level signal based at least in part on the weighted first motion detection signal and the weighted second motion detection signal. The computer-readable medium may include code for causing the computer to compare the motion level signal with a motion event threshold and store a time period of the sequence of images responsive to the motion level signal exceeding the motion event threshold.

BRIEF DESCRIPTION OF THE DRAWINGS

A further understanding of the nature and advantages of the present invention may be realized by reference to the following drawings. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

Figure 1:
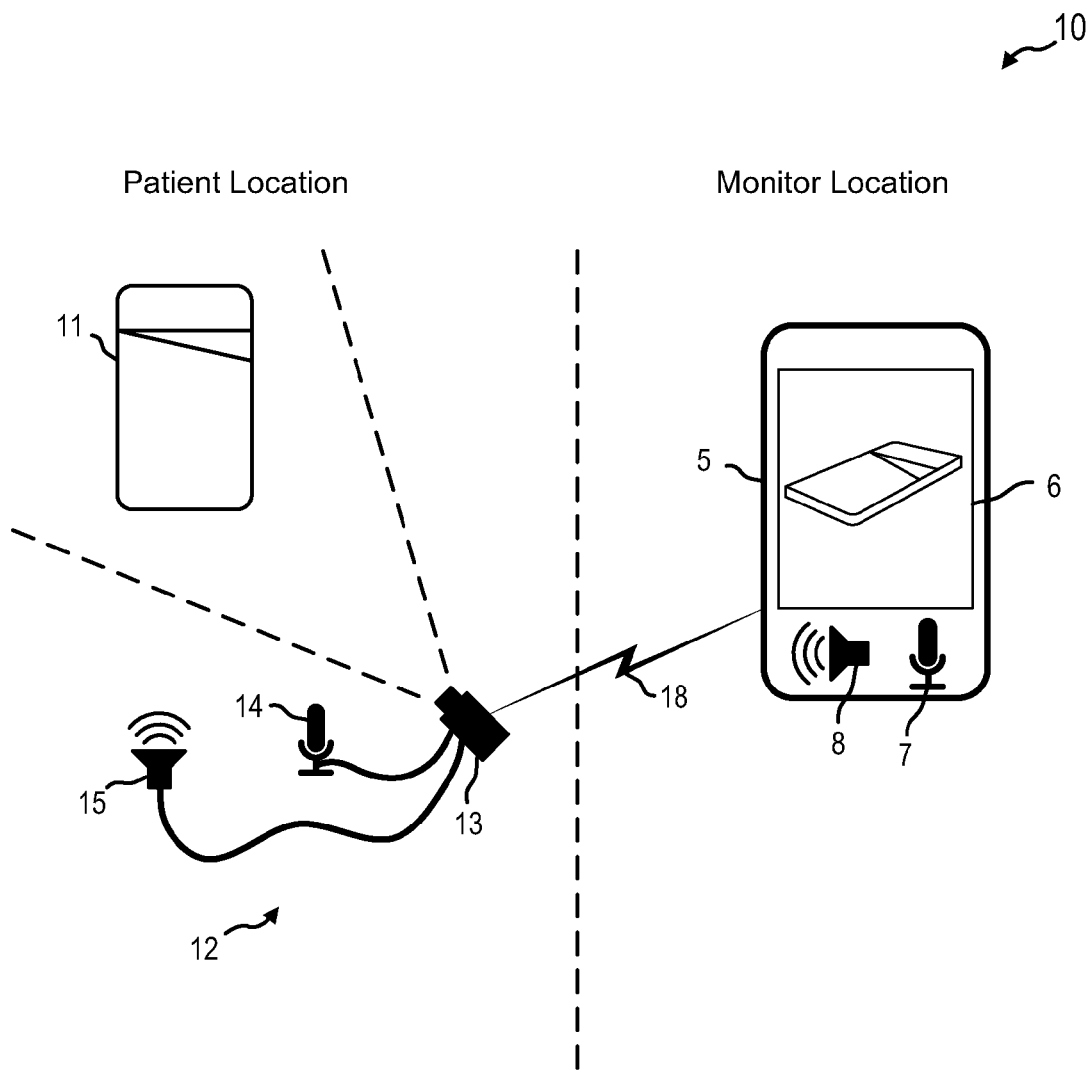
FIG. 1 illustrates an activity monitor system in accordance with various embodiments.

FIG. 1 illustrates an activity monitor system 10 for monitoring a patient in accordance with various embodiments. Activity monitor system 10 may include a sensor system 12 in a patient location that is positioned to monitor an area of interest 11 (e.g., crib, bed, etc.) and a monitoring device 5 in another location (e.g., different room, etc.). Sensor system 12 may include a video camera 13 and a microphone 14, positioned such that the video camera 13 is pointed at the area of interest 11 and the microphone 14 can pick up sound from the area of interest 11. Optionally, sensor system 12 may include a speaker 15. The monitoring device 5 may have a display device 6, microphone 7, and/or a speaker 8. The monitoring device 5 and the sensor system 12 can communicate with each other through a connection 18 (e.g., wired or wireless connection).

In embodiments, activity monitor system 10 detects "interesting events" based on data from sensor system 12 and performs actions based on detecting the events. The activity monitor system 10 may detect interesting events based on video processing of a substantially live sequence of images from the video camera 13. The activity monitor system 10 may detect events based on other sensors and may use a combination of sensor data to detect events. The activity monitor system 10 may store event data from the one or more sensors (e.g., video, audio, etc.) for interesting events and/or trigger an alarm action. Alarm actions may include sounding an audible alarm at the monitoring device 5. Alarm actions may also include enabling a substantially live video display from video camera 13 on display device 6 and/or reproduction of substantially live audio from microphone 14 to speaker 8 on monitoring device 5 concurrently with the audible alarm.

Activity monitor system 10 may use video processing techniques such as motion estimation and multi-region processing to detect events. Event detection may include integrating motion levels from one or more regions to determine a motion alert level. Comparing the motion alert level with one or more thresholds may trigger various actions such as recording the event and/or performing an alarm action. Multi-region processing may include suppressing event detection and/or alarm generation based on motion in one or more regions, motion transitions, and/or motion entry and/or exit points. The activity monitor system 10 may use other sensor information such as an audio signal to detect events. The activity monitor system 10 may include a user interface to allow customization of event detection and/or behavior upon detecting events. In embodiments, the activity monitor system is implemented using a smartphone and a wireless network camera.

This description provides examples, and is not intended to limit the scope, applicability or configuration of the invention. Rather, the ensuing description will provide those skilled in the art with an enabling description for implementing embodiments of the invention. Various changes may be made in the function and arrangement of elements. Thus, various embodiments may omit, substitute, or add various procedures or components as appropriate. For instance, it should be appreciated that the methods may be performed in an order different than that described, and that various steps may be added, omitted or combined. Also, aspects and elements described with respect to certain embodiments may be combined in various other embodiments. It should also be appreciated that the following systems, methods, devices, and software may individually or collectively be components of a larger system, wherein other procedures may take precedence over or otherwise modify their application.

Figure 2:
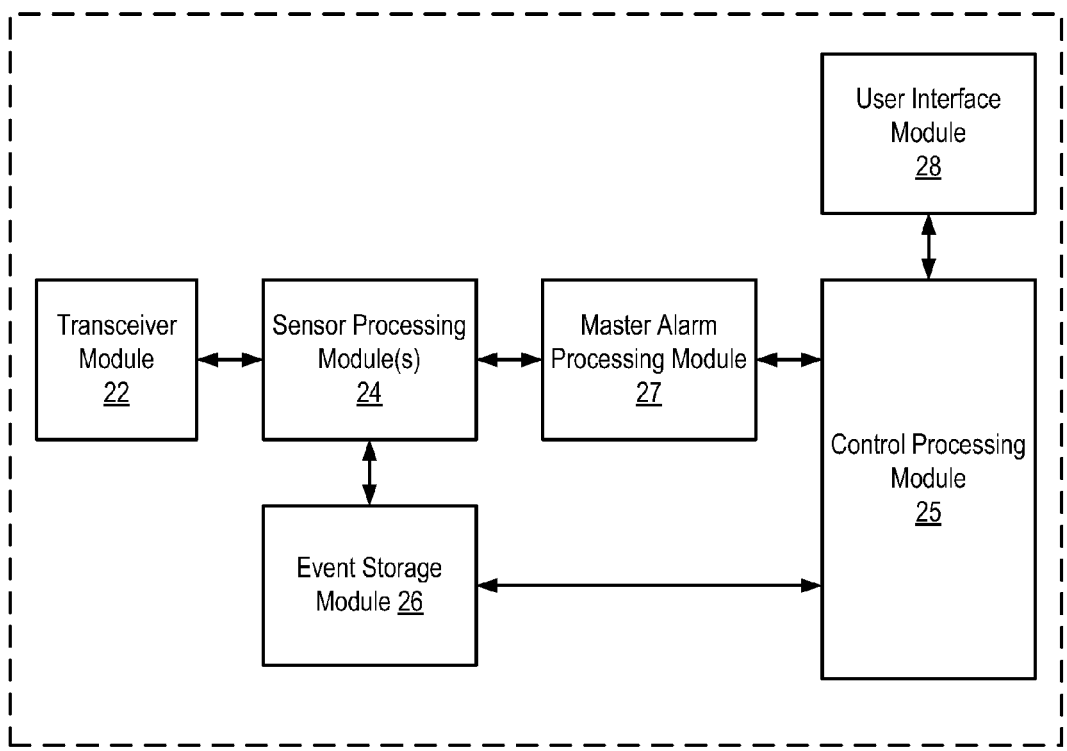
FIG. 2 illustrates a device for monitoring an area of interest in accordance with various embodiments.

FIG. 2 illustrates a block diagram of an activity monitor device 20 for detecting and responding to events of interest in accordance with various embodiments. Device 20 may be an example of the monitoring device 5 of activity monitor system 10, or, in some embodiments, one or more of the components of device 20 may be a part of the sensor system 12. In one embodiment, activity monitor device 20 is implemented as a computing device such as a smartphone, tablet, netbook, and/or other computing device. Activity monitor device 20 may include a transceiver module 22, sensor processing module 24, control processing module 25, event storage module 26, master alarm processing module 27, and/or user interface module 28. User interface module 28 may include components for accepting user input and displaying output (e.g., display, keyboard, touch-screen, microphone, speaker, virtual keyboard, etc.) and interpreting user events (e.g., touch screen controller, etc.). For example, user interface module 28 may include display screen 6 (which may be a touch-screen display device), microphone 7, and/or speaker 8 of monitoring device 5. Each of these components may be in communication with each other.

Transceiver module 22 may receive communications from other systems and/or devices such as sensor system 12. For example, the transceiver module 22 may receive a substantially live data stream from sensor system 12 via connection 18. The sensor processing module 24 may process the received sensor data stream and determine "interesting events" that warrant actions by the device 20 and/or sensor system 12. For example, the sensor processing module 24 may process a video stream received from camera 13 to detect motion events. The sensor processing module 24 may also receive an audio signal from microphone 14 and process the audio signal to detect sound patterns. Sensor processing module 24 may receive and process other data from additional sensors of sensor system 12. Sensor processing module 24 may determine, based on the received sensor data, that an event of interest is occurring. Sensor processing module 24 may determine that the sensor data for the event be recorded in event storage module 26 for later review. Sensor processing module 24 may also determine that an alarm action should be performed in response to the detected event and may perform corresponding alarm actions. For example, sensor processing module 24 may generate an alarm, enable a substantially live video display, and/or enable a substantially live audio feed through user interface 28 from sensor system 12 (e.g., via display device 6 and/or speaker 8 of monitoring device 5).

Control processing module 25 may receive user input through user interface 28 for controlling sensor processing module 24 and/or event storage module 26. For example, control processing module 25 may receive alarm detection settings, event recording settings, and/or commands for retrieving the recorded events from the event storage module 26. Master alarm processing module 27 may determine appropriate alarm actions based on the detected alarm events.

These components may, individually or collectively, be implemented with one or more Application Specific Integrated Circuits (ASICs) adapted to perform some or all of the applicable functions in hardware. Alternatively, the functions may be performed by one or more other processing units (or cores), on one or more integrated circuits. In other embodiments, other types of integrated circuits may be used (e.g., Structured/Platform ASICs, Field Programmable Gate Arrays (FPGAs) and other Semi-Custom ICs), which may be programmed in any manner known in the art. The functions of each unit may also be implemented, in whole or in part, with instructions embodied in a memory, formatted to be executed by one or more general or application-specific processors.

Figure 3:
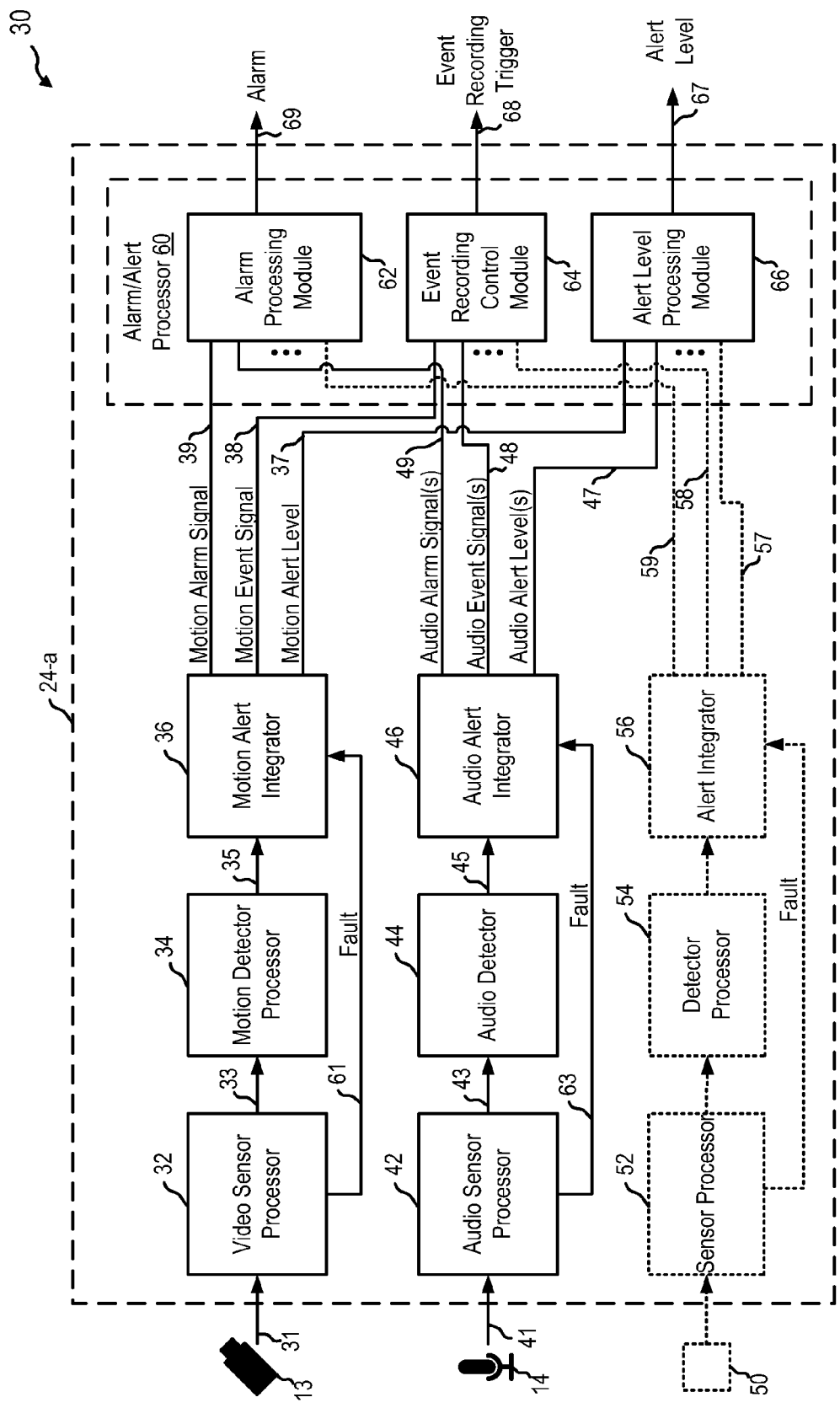
FIG. 3 is a block diagram illustrating processing elements of an activity monitor system in accordance with various embodiments.

FIG. 3 is a block diagram that illustrates processing system 30 for performing activity monitoring in accordance with various embodiments. Processing system 30 may illustrate, for example, various processing elements of a sensor processing module 24-a, which may perform the functions of sensor processing module 24 of FIG. 2. Processing system 30 may include components to process information from sensor system 12 and trigger event recording and/or generate alarm/alert signals based on the sensor information. For example, processing system 30 may include components to process video images from video camera 13, an audio signal from microphone 14, and/or signals from other sensors 50.

In embodiments, processing system 30 includes components for processing a sequence of images including video sensor processor 32, motion detector processor 34, and/or motion alert integrator 36. In embodiments, video sensor processor 32 is configured to receive images of a substantially live video stream 31 from the video camera 13 (e.g., via transceiver module 22, etc.). The rate that images may be transferred from video camera 13 to video sensor processor 32 may typically be in the range of one to thirty images per second (i.e., 1-30 Hz). However, in various embodiments the rate may be lower or higher than 1-30 Hz, and may be selectable. The video sensor processor 32 may split each received image into one or more different, arbitrarily shaped overlapping or non-overlapping regions. One way to accomplish this is to apply a mask to the image, with the mask passing unchanged the pixels of interest, and zeroing the region's excluded pixels. Each region may have a different mask, creating multiple images, one for each region. Other standard image processing operations such as noise removal or contrast enhancement can also be applied, either before the images are split, or after. These processed images 33 are passed on to the motion detector processor 34.

In embodiments, motion detector processor 34 performs multi-region processing on the images 33 from the video sensor processor 32. For example, the motion detection processor 34 may compare the image received for each region with the previously received image and produce a number (the Motion Level) representing the amount of change that has occurred in each region. There are a number of techniques for doing this, one is to subtract the image from the previous one, then sum the values of the individual pixels in the resulting image. The result is a numeric Motion Level Value for each region. One of these regions, typically the central region, may be designated the Primary Region. These region Motion Levels 35 are then passed on to the motion alert integrator 36.

The purpose of the motion alert integrator 36 is to filter out short duration motion, and to only trigger event recording and/or alarm generation if the duration and/or location of the motion warrants it. In embodiments, the motion alert integrator 36 uses the Motion Level Values 35 for each region to generate a single integer Motion Alert Level signal 37, a single Motion Event Signal 38, and/or a single Motion Alarm signal 39 for triggering event recording and/or alarm actions based on the detected motion events.

Processing system 30 may also include components to process and generate alarm/alert conditions based on audio from a microphone 14. For example, a microphone 14 may convert audio into an audio signal 41 that is fed into the audio sensor processor 42 (e.g., via transceiver 22, etc.). The audio sensor processor 42 may apply one or more processing algorithms to remove interfering noises. For example, the audio sensor processor 42 may use equalization and/or adaptive noise cancellation techniques. The audio sensor processor 42 then passes the processed signal 43 in the form of sequential samples to the audio detector 44. The audio detector may pass an accumulated maximum value of the samples to the audio alert integrator 46 as the Audio Meter signal 45.

Like the motion alert integrator 36, the purpose of the audio alert integrator 46 is to only generate an alarm signal if the level and duration of the Audio Meter signal 45 warrants it.

For example, periodic, momentary sounds may indicate a baby is awake but not in distress, whereas a continuous sound above a threshold could indicate crying and a need for attention. Detecting sound below a threshold may also be useful, for example, in the case where the microphone is sensitive enough to pick up the sound of breathing, and the absence of audio should trigger an alarm. Therefore, audio alert integrator 46 may generate one or more Audio Alert Level signals 47 (e.g., High and Low Audio Alert Level signals), one or more Audio Event Signals 48 (e.g., High and Low Audio Event Signals), and/or one or more Audio Alarm Signal(s) 49 (e.g., High Audio Alarm Signal and/or Low Audio Alarm Signal). Generation of these signals by the audio sensor processor 42, audio detector 44, and/or audio alert integrator 46 is described in more detail below.

Additional sensors 50, if present, may follow similar processing steps 52, 54, 56, each resulting in additional Alert Level signals 57, Event signals 58, and Alarm signals 59. Examples of additional sensors that may be used with activity monitor system 10 include, but are not limited to, video cameras, still cameras, web cameras, infra-red cameras, microphones, infra-red motion sensors, vibration sensors, heart rate sensors, blood oxygen sensors, electroencephalography (EEG) sensors, ultrasonic sensors, laser distance sensors, breath sensors, light level sensors, and/or pressure sensors.

Another function of the sensor processors is to determine if the corresponding sensor is faulty. Examples of a faulty sensor would be loss of wireless connection, no signal being received, continuous non-varying signal, or an out of range signal. The resulting sensor fault signal (Video Sensor Fault 61, Audio Sensor Fault 63, etc.) is passed to the corresponding Alert Integrator and may be used to suppress the associated event/alarm signal (Motion Alarm, Audio Alarm, etc). For example, if the sensor is in a fault state, no Alarm signal associated with that sensor may be generated. Sensor faults may also be reported through the user interface using a visible sensor fault indicator or generating a sensor fault alarm.

All of the alert and alarm signals are passed to the alarm/alert processor 60. Alarm/alert processor 60 may include an alarm processing module 62, an event recording control module 64, and/or an alert level processing module 66. The alarm processing module 62 may receive the alarm signals from each of the sensor integrator modules and generate a single Alarm signal 69 (e.g., using an "OR" logic operation, etc.). For example, if any of the received alarm signals (e.g., Motion Alarm Signal 39, Audio Alarm Signal(s) 49, etc.) are ON, then alarm processing module 62 may set Alarm signal 69 to ON. Otherwise Alarm signal 69 may be set to OFF. The alarm processing module 62 may use other functions. For example, the alarm processing module 62 may only set Alarm signal 69 to ON based on some combination of the received alarm signals. The Event signals may be similarly combined in event recording control module 64. For example, the event recording control module 64 may receive the Event signals from each of the sensor integrator modules and generate a single Event Recording signal 68 (e.g., using an "OR" logic operation, etc.) used to trigger recording of the event as described in more detail below. The Alert Level signals may also be combined in alert level processing module 66 to generate a single Alert Level signal 67 (e.g., using a "maximum" arithmetic function). For example, Alert Level signal 67 may be set to the maximum of all of the received alert level signals (such as the Motion Alert Level 37, Audio Alert Level(s) 47, etc.).

When the Alarm signal 69 is set to ON, one or more Alert Level signals may be stored and/or displayed to show the level of activity that triggered the alarm. One or more of the Alert Level signals may also be stored when event recording is triggered. For example, when event recording is triggered, Alert Level signal 67 may be stored with the event recording to show the Alert Level associated with the event. Alternately, individual sensor Alert Level signals (e.g., Motion Alert Level 37, Audio Alert Level 47, etc.) may be stored and associated with the event (e.g., for later display in connection with reviewing the event, etc.).

Figure 4:
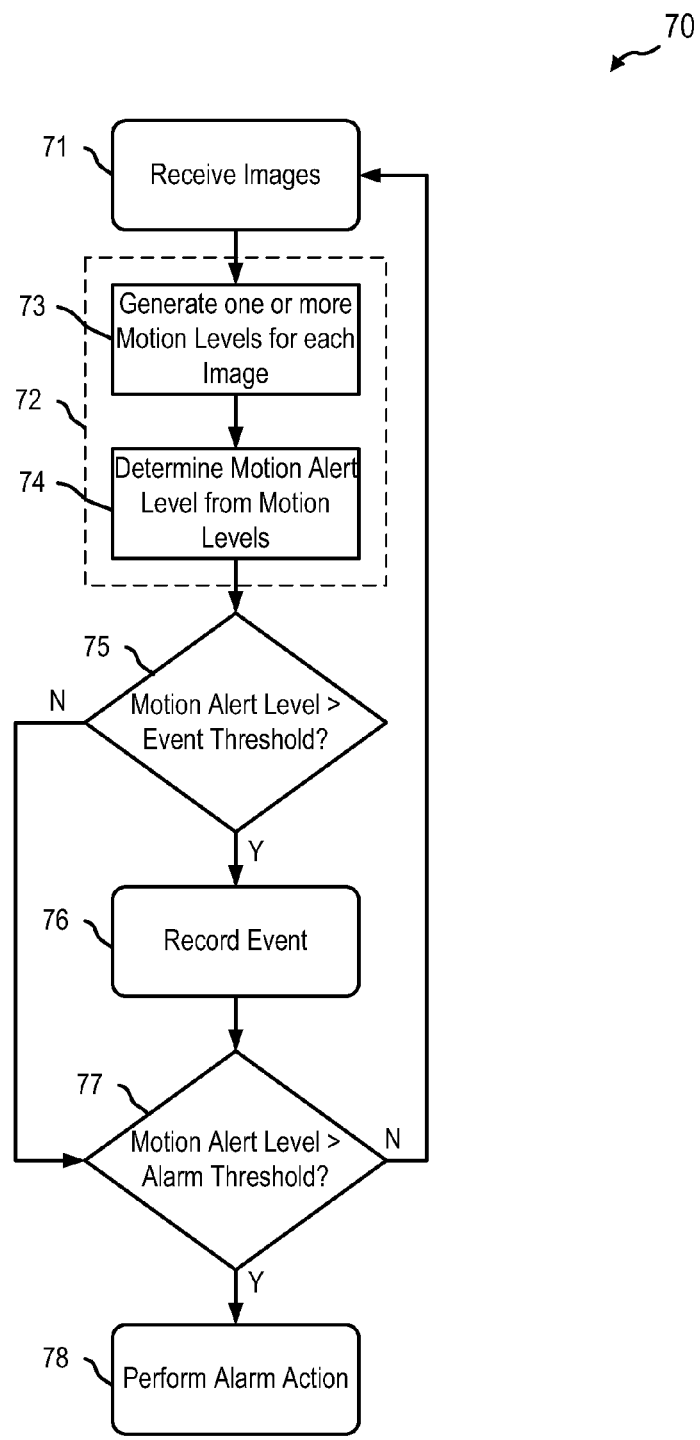
FIG. 4 is a functional block diagram of a method for processing images to generate an alarm and/or store events based on detected motion in accordance with various embodiments

FIG. 4 is a functional block diagram of a method 70 for processing images to generate an alarm and/or store events based on detected motion in accordance with various embodiments. Method 70 may be performed, for example, by sensor processing modules 24 of FIG. 2 and/or FIG. 3. For example, method 70 may illustrate processing performed by video sensor processor 32, motion detector processor 34, and/or motion alert integrator 36 of FIG. 3.

Method 70 starts at block 71 where images are received. For example, sensor processing module 24 may receive a substantially live sequence of images from a video camera 13. At block 72, each image may be processed to detect motion in one or more regions and a Motion Alert Level may be determined based on the sequence of images.

Block 72 may include generating one or more motion levels (e.g., motion levels for each region) at block 73 and determining the Motion Alert Level from the motion levels for the regions at block 74.

At block 75, the Motion Alert Level is compared with a Motion Event Threshold. If the Motion Alert Level exceeds the Motion Event Threshold, the method 70 may proceed to block 76 where the event is recorded (e.g., recording of the event is started). At block 77, the Motion Alert Level is compared with a Motion Alarm Threshold. If the Motion Alert Level exceeds the Motion Alarm Threshold, the method 70 may proceed to block 78 where an alarm action is performed (e.g., generate an audible alarm, enable a live video display, etc.).

Figure 5:
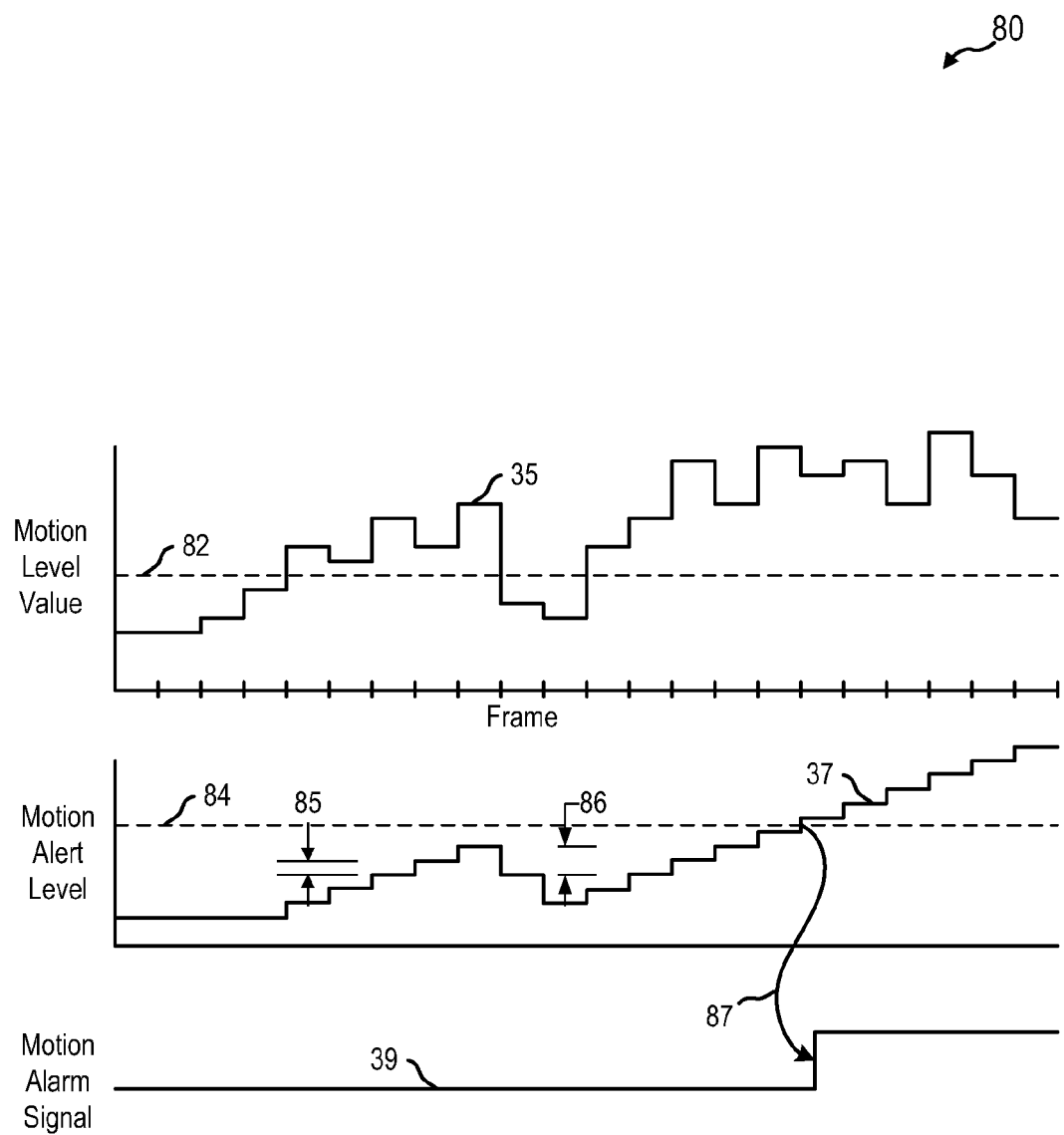
FIG. 5 shows a timing diagram that illustrates an example of motion detection and evaluation for a single region in accordance with various embodiments.

One implementation uses the Motion Level Value 35 for a single region. FIG. 5 shows a timing diagram 80 that illustrates an example of generating Motion Alarm Signal 39 from a Motion Level Value 35 for a single region in accordance with various embodiments. The motion detector processor 34 may process each incoming image in a sequence of images and generate a Motion Level Value 35 for each image (e.g., for the Primary Region). The motion alert integrator 36 may use a function based on the Motion Level Value 35 that accounts for the amplitude and/or time duration of motion associated with multiple incoming images of the sequence of images to determine the Motion Alert Level 37. In embodiments, the motion alert integrator 36 uses an integrating function of the Motion Level Value 35 to determine the Motion Alert Level 37.

In embodiments, the motion alert integrator 36 compares the Motion Level Value 35 against a Motion Threshold 82 for each image. If the Motion Level Value 35 is greater than the Motion Threshold 82, the Motion Alert Level 37 may be incremented (e.g., by a Motion Alert Increment Value 85, etc.). If it is below the Motion Threshold 82, the Motion Alert Level 37 may be decremented (e.g., by a Motion Alert Decrement Value 86, etc.). In embodiments, the rate of increase of the Motion Alert Level 37 may be different than the rate of decrease. For example, FIG. 5 illustrates that the Motion Alert Level Decrement Value 86 may be a larger step (i.e., in absolute value) per frame than the Motion Alert Increment Value 85. This may, for example, decrease sensitivity to motion that is intermittent. However, the Motion Alert Level Increment Value 85 may be larger or the same as the Motion Alert Level Decrement Value 86 in other embodiments. In embodiments, the Motion Alert Level 37 has preset maximum and minimum values. For example, continued motion may not increment the Motion Alert Level 37 past the preset maximum value while the preset minimum prevents lack of motion from continuously decrementing the Motion Alert Level 37. The motion alert integrator 36 may use other integrating functions that generate a numeric Motion Alert Level 37 from the Motion Level Value 35 for multiple incoming images of a video stream (e.g., moving average filter, integrating filter, etc.).

If the Motion Alert Level 37 reaches a Motion Alert Threshold 84, the Motion Alarm Signal 39 may be set to ON (e.g., high level, etc.). Otherwise the Motion Alarm Signal 39 may be set to OFF (e.g., low level, etc.). For example, arrow 87 indicates setting the Motion Alarm Signal 39 to ON based on the Motion Alert Level 37 exceeding the Motion Alert Threshold 84. Various alarm actions may be triggered when the Motion Alarm Signal 39 is set to ON, as described in more detail below.

Figure 6:
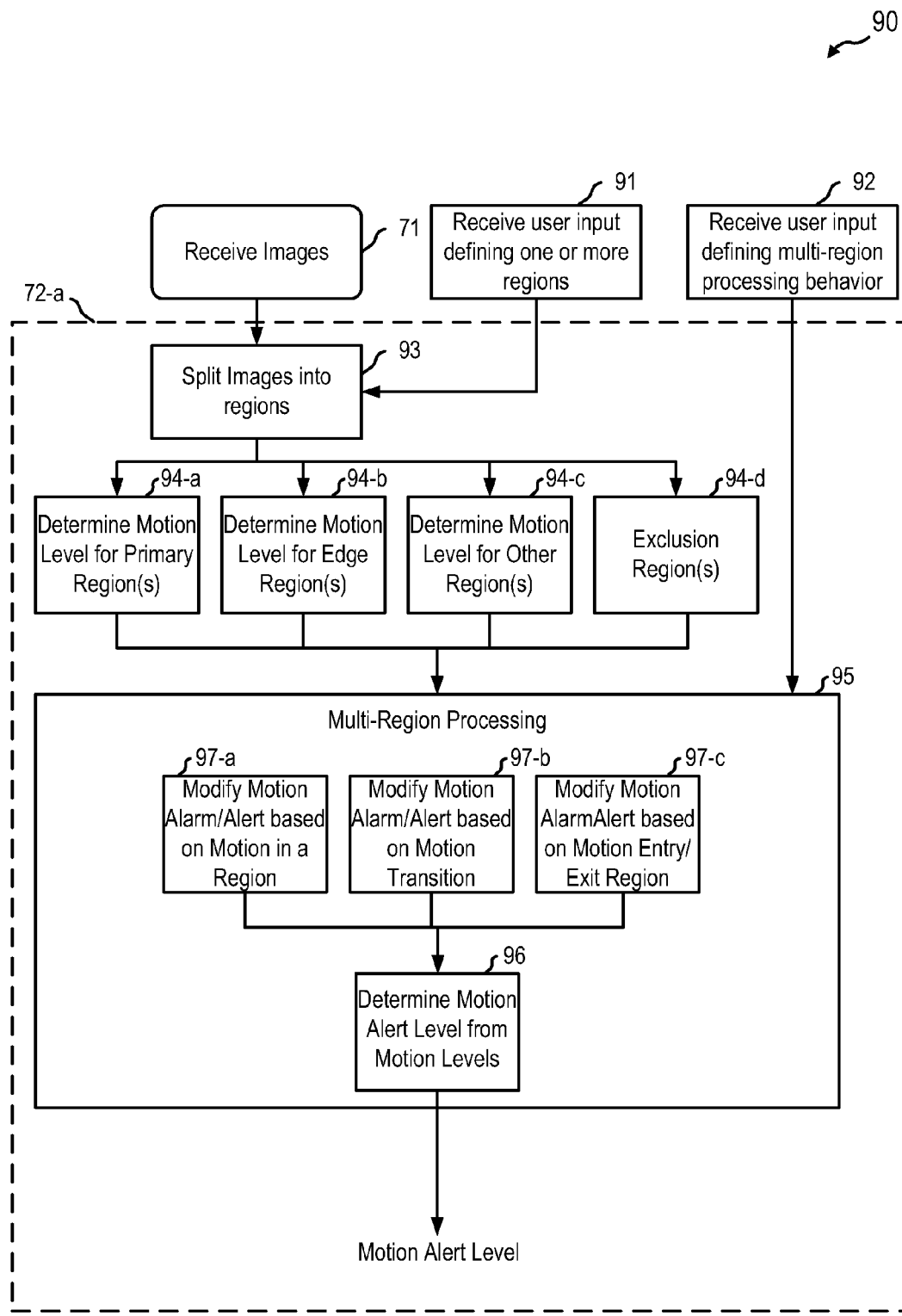
FIG. 6 is a functional block diagram of a method utilizing multi-region processing to generate an alarm and/or trigger storing of events based on detected motion in accordance with various embodiments.

In embodiments, the motion alert integrator 36 uses multi-region processing to generate the Motion Event Signal 38 and/or Motion Alarm Signal 39 from two or more Motion Level Values 35 representing motion from two or more regions of the incoming images. Multi-region processing may be useful where motion in one area, motion transitions, motion entry points, and/or motion exit points should modify recognition of events for recording and/or triggering alarm actions. FIG. 6 is a functional block diagram of a method 90 for using multi-region processing to recognize activity events in accordance with various embodiments. Method 90 may be used in conjunction with method 70 of FIG. 4. For example, block 72-*a* may illustrate multi-region processing used in method 70.

In method 90, user input defining one or more regions may be received at block 91. For example, a user may define a Primary Region, one or more Edge Regions, one or more Exclusion Regions, and/or other regions. Alternatively, regions may be defined using various automatic features such as detection of regions of motion. Receiving user input and/or automatic region definition is described in more detail below.

At block 93, incoming images may be split into regions according to the defined regions. For example, masking may be used to create multiple images from each incoming image, one for each region. At blocks 94(*a-d*), motion levels may be determined for each region. For example, the techniques for motion estimation described above may be used to generate a Motion Level Value 35 for each region.

Figure 7A:
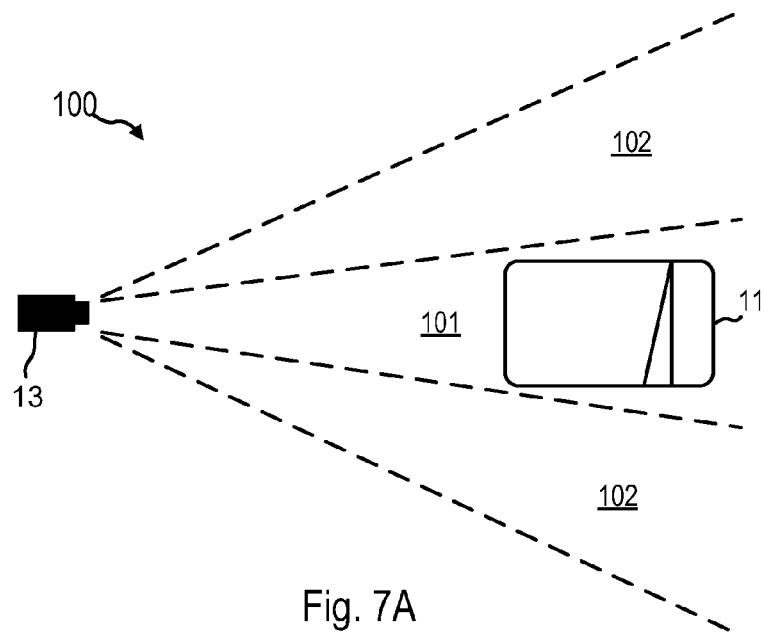
FIG. 7A is a diagram of monitoring a patient location with multiple image regions in accordance with various embodiments.

Multi-region processing may be used at block 95 based on the Motion Level Values 35 and user input received at block 92 defining the multi-region processing behavior. Multi-region processing may include, for example, suppressing a motion alarm and/or alert (e.g., suppressing generation of the Motion Alert Level Signal 37, the Motion Event Signal 38, and/or the Motion Alarm Signal 39) based on motion in one or more regions at block 97-*a*. For example, FIG. 7A is a diagram 100 of a case where the central part of the image from video camera 13 contains a crib 11. Two regions may be identified, a Primary Region 101 that is limited to the central area, including the crib 11, and an Edge Region 102 that contains everything not in the Primary Region 101. If there is motion in the Edge Region 102, this may indicate that a parent is attending the child in the crib 11, and no alarm should be generated. If, however, there is motion in the Primary Region 101 only, an alarm should be allowed to be generated based on the motion level in the Primary Region 101.

Figure 7B:
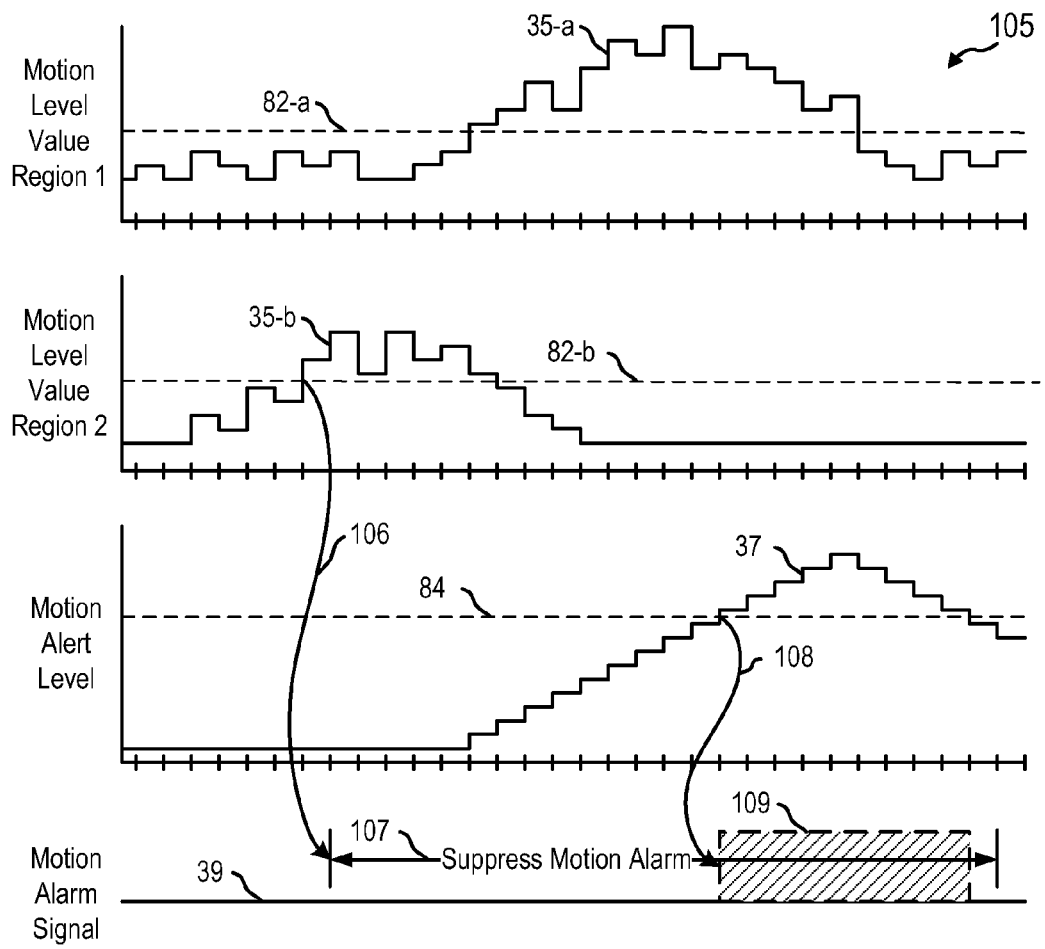
FIG. 7B is a timing diagram that illustrates suppression of the alarm signal based on multi-region processing in accordance with various embodiments.

FIG. 7B is a timing diagram 105 that illustrates suppression of the Motion Alarm Signal 39 based on motion in Edge Region 102 in accordance with various embodiments. In timing diagram 105, motion detector processor 34 generates Motion Level Value 35-*a* for Primary Region 101 and Motion Level Value 35-*b* for Edge Region 102. The motion alert integrator 36 may compare Motion Level Value 35-*a* against a Motion Threshold 82-*a* and Motion Level Value 35-*b* against a Motion Threshold 82-*b*. Motion Threshold 82-*a* and Motion Threshold 82-*b* may be the same value or different values in various embodiments. The motion alert integrator 36 may generate Motion Alert Level 37 based on one or more Motion Level Values 35. In the simplest case, Motion Alert Level 37 may be based on Motion Level Value 35-*a* for Primary Region 101. As illustrated in timing diagram 105, motion in Edge Region 102 may exceed Motion Threshold 82-*b* at time 106. The motion alert integrator 36 may suppress Motion Alarm Signal 39 for a time period 107 after Motion Level Value 35-*b* exceeds the Motion Threshold 82-*b*. The time period 107 for suppression of motion events in the Primary Region 101 may be selectable. As illustrated in timing diagram 105, when Motion Alert Level 37 exceeds the Motion Alert Threshold 84 at time 108, Motion Alarm Signal activation 109 may be suppressed and no alarm will be generated based on the corresponding motion event in the Primary Region 101.

Returning to FIG. 6, other multi-region processing techniques may be used. For example, a motion transition from one region to another region may be detected and motion alarm and/or alert behavior may be modified based on the motion transition at block 97-*b*. For example, the motion alarm and/or alert conditions may be explicitly triggered or suppressed based on these detected motion transitions. Block 97-*b* may account for the motion velocity in determining how to process the motion transition. For example, a relatively rapid transition from the Primary Region to an Edge Region may indicate that a patient has intentionally arisen and left the room while a slower region transition may be indicative of different behavior.

A point of entry and/or exit of motion within the image frame may also be detected and used to modify the motion alarm and/or alert behavior at block 97-*c*. For example, if motion begins in an Edge Region (e.g., the first detected motion is in the Edge Region), it may indicate that someone has entered the room to tend to the patient. If motion begins in the Primary Region and subsequently transitions to an Edge Region, and then ceases (e.g., the last detected motion is in the Edge Region), it may indicate that the patient has left the room. The motion alarm and/or alert conditions may be explicitly triggered or suppressed based on these detected motion entry and/or exit points.

At block 96, the Motion Alert Level may be generated using the Motion Levels from one or more regions and the multi-region processing performed at blocks 97(*a-c*). The Motion Alert Level may be based on one region (e.g., the Primary Region, etc.) or, in embodiments, may be based on the Motion Levels from multiple regions by combining weighted Motion Levels from each region. For example, each region may have a weighting coefficient applied and the weighted Motion Levels may be combined to generate the Motion Alert Level. In one embodiment, weighting coefficients range from −1 to +1 where a weight of 0 means the region will be ignored and a negative weight means that motion in the corresponding region will suppress the Motion Alert Level.

In embodiments, multi-region processing of the Motion Alert Level may use information from other sensors. For example, audio sensor information (e.g., Low Audio Alert Level, High Audio Alert Level, etc.), may be considered a region and may be factored into the Motion Alert Level (e.g., with an applied weighting coefficient). In embodiments, the region weighting coefficients vary temporally based on motion in various regions. For example, motion in one region may affect the weighting coefficients of one or more other regions for a period of time. Other combinations of 2 or more regions and/or combinations of the above techniques are possible and the motion alert integrator 36 can be programmed to handle a variety of regional motion scenarios.

Figure 8:
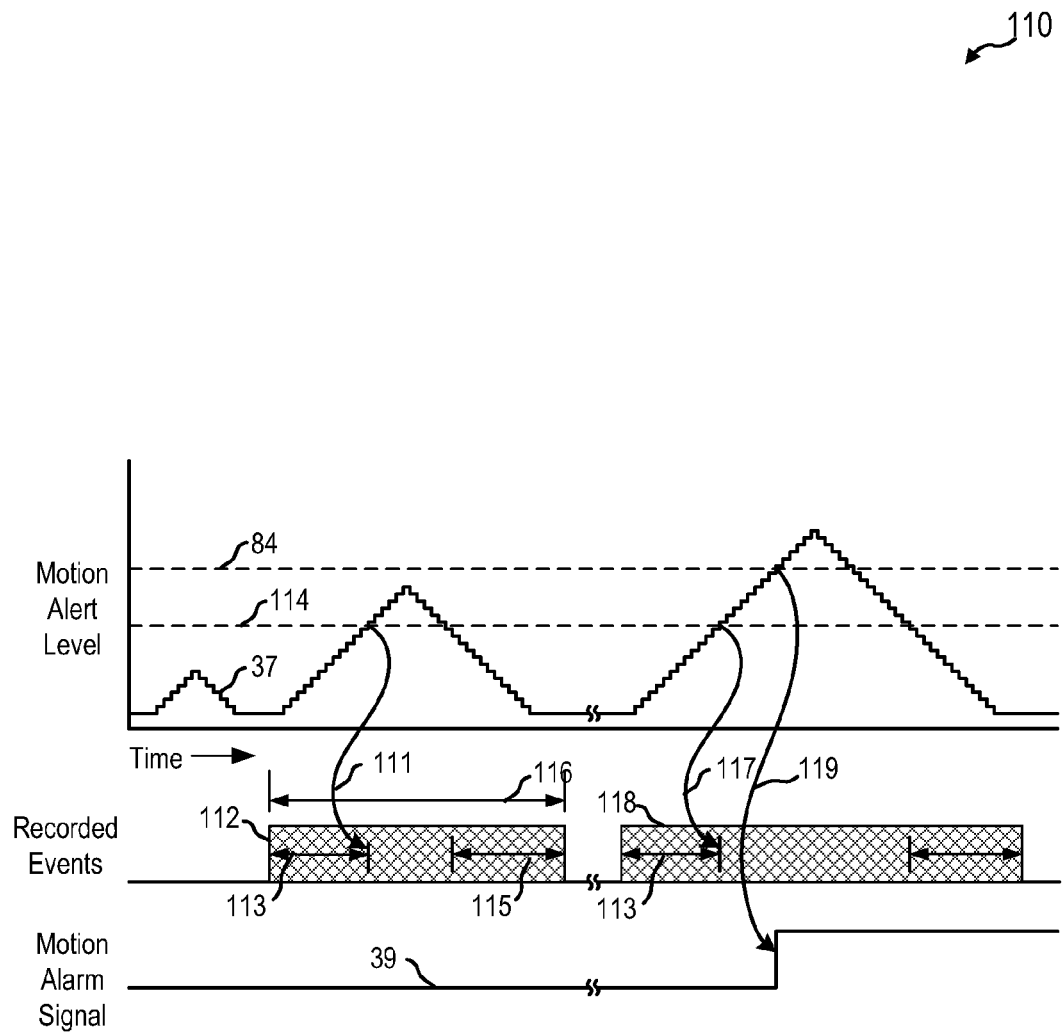
FIG. 8 is a timing diagram that illustrates the use of separate thresholds for event recording and/or alarm triggering in accordance with various embodiments.

As described above, the activity monitor may use different thresholds for triggering event recording and performing alarm actions. FIG. 8 shows a timing diagram 110 that illustrates the use of separate thresholds for event recording and/or alarm/alert triggering in accordance with various embodiments. In timing diagram 110, Motion Alert Threshold 84 may trigger an alarm/alert action while Motion Event Threshold 114 may trigger recording of an event for subsequent viewing using the activity monitor system 10 (e.g., via display 6 of monitoring device 5).

In timing diagram 110, a first motion event may cause Motion Alert Level 37 to exceed Motion Event Threshold 114 at an event trigger time 111. As illustrated in timing diagram 120, the activity monitor system may capture the event as illustrated by recorded event 112. Recorded event 112 may include some amount of data from prior to event trigger time 111. For example, activity monitor system 10 may be continuously recording sensor data (e.g., video images, audio data, etc.) to a buffer and storing a predetermined time period of the sensor data. When the event trigger time 111 occurs, the data in the buffer may be stored along with additional sensor data that occurs after the event trigger time 111.

Various settings may be used to determine the total duration 116 of the recording 112. For example, "pre-alarm" time 113 may specify the amount of data to be stored with the recording 112 prior to the event detection 111. A "post-alarm" time 115 may specify the length of time to continue recording after the Motion Alert Level 37 drops below the Motion Event Threshold 114. In addition or alternatively, minimum and/or maximum recording times may be specified. For example, the activity monitor system 10 may record until the earliest occurring of the expiration of the post-event timer 115 or a maximum recording time.

Timing diagram 110 illustrates a second motion event in which Motion Alert Level 37 exceeds the Motion Event Threshold 114 at an event trigger time 117 and exceeds the Motion Alert Threshold 84 at a time 119. As illustrated in timing diagram 120, the second motion event may trigger recording of the event 118 and triggering of the Motion Alarm Signal 39. A corresponding alarm action may be stored with the recorded event. For example, an indicator of the alarm action performed in response to the Motion Alarm Signal 39 at time 119 may be stored with the event recording 118 for later review.

Figure 9:
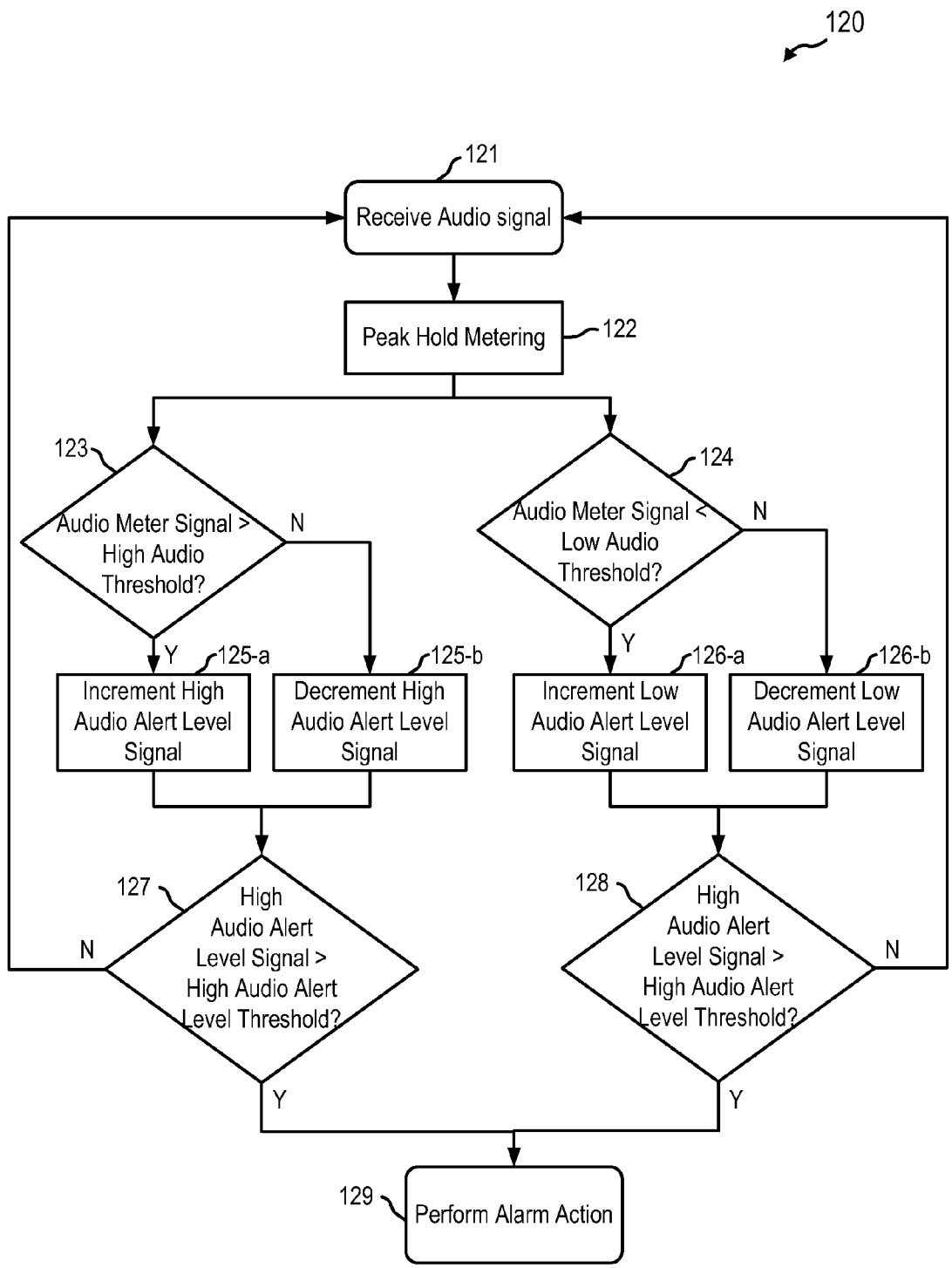
FIG. 9 is a functional block diagram of a method for processing audio to generate an alarm and/or store events in accordance with various embodiments.

FIG. 9 is a functional block diagram of a method 120 for processing audio to generate an alarm and/or store events in accordance with various embodiments. Method 120 may be performed, for example, by sensor processing modules 24 of FIG. 2 and/or FIG. 3. Method 120 may illustrate, for example, audio processing performed by audio sensor processor 42, audio detector 44, and/or audio alert integrator 46 as illustrated in FIG. 3.

Method 120 may begin at block 121, where an audio signal is received (e.g., audio signal 41 received at audio sensor processor 42 from microphone 14 as illustrated in FIG. 3). At block 122, the audio detector 44 may perform a peak hold metering function on the audio signal 43. One implementation of a peak hold meter is to compare the level of each sample to a saved maximum value and replace the maximum value with the sample value if the sample value is higher. On a periodic basis (e.g., once per second, etc.) the accumulated maximum value is passed to the audio alert integrator 46 and then reset to zero. This is the Audio Meter signal 45.

The audio alert integrator 46 compares the Audio Meter signal 45 received from the audio detector 44 to one or more thresholds to detect the presence or absence of sound. In embodiments, the audio alert integrator 46 may detect the presence of sound above a certain level for a certain duration and/or sound below a threshold for a certain duration and trigger event recording and/or alarm conditions based on either condition (e.g., according to a user setting). For example, the audio alert integrator 46 may compare the Audio Meter signal 45 to a first threshold (e.g., a High Audio Threshold) to detect High Audio Alert conditions at block 123. If the level exceeds the High Audio Threshold, a High Audio Alert Level signal may be incremented at block 125-a. Otherwise, the High Audio Alert Level signal is decremented at block 125-b. The High Audio Alert Level signal may have preset maximum and minimum values (e.g., not incremented beyond a High Audio Alert Maximum value and not decremented beyond a High Audio Alert Minimum value). If, at block 127 the High Audio Alert Level signal exceeds a threshold (e.g., High Audio Alert Threshold), an action may be performed at block 129. For example, the Audio Event Signal 48 and/or a High Audio Alarm signal 49 may set to ON to trigger event recording and/or an alarm action.

The audio alert integrator 46 may also compare the Audio Meter signal 45 to another threshold (e.g., Low Audio Threshold) at block 124. If the level is below the Low Audio Threshold, a Low Audio Alert Level signal is incremented at block 126-a Otherwise, the Low Audio Alert Level signal is decremented at block 126-b. Similar to the High Audio Alert Level signal, the Low Audio Alert Level signal may have preset maximum and minimum values (e.g., not incremented beyond a Low Audio Alert Maximum value and not decremented beyond a Low Audio Alert Minimum value). If the Low Audio Alert Level signal exceeds the Low Audio Alert Threshold at block 128, an action may be performed at block 129. For example, the Audio Event Signal 48 or a Low Audio Alarm signal 49 may set to ON to trigger event recording and/or an alarm action. This Low Audio Alarm may be useful in the case where the microphone is sensitive enough to pick up the sound of breathing, and the absence of audio should trigger an alarm.

Multiple locations, each with their own set of sensors may be monitored simultaneously. Each location may be configured with a unique set of thresholds and sensor processing. Each location may be processed independently and may generate its own Alert Level and Alarm signals. The master alarm processing module 27 may combine these location Alarms into a single Master Alarm. If any location Alarm is TRUE, then the Master Alarm may be set to TRUE, otherwise it may be FALSE.

Figure 10:
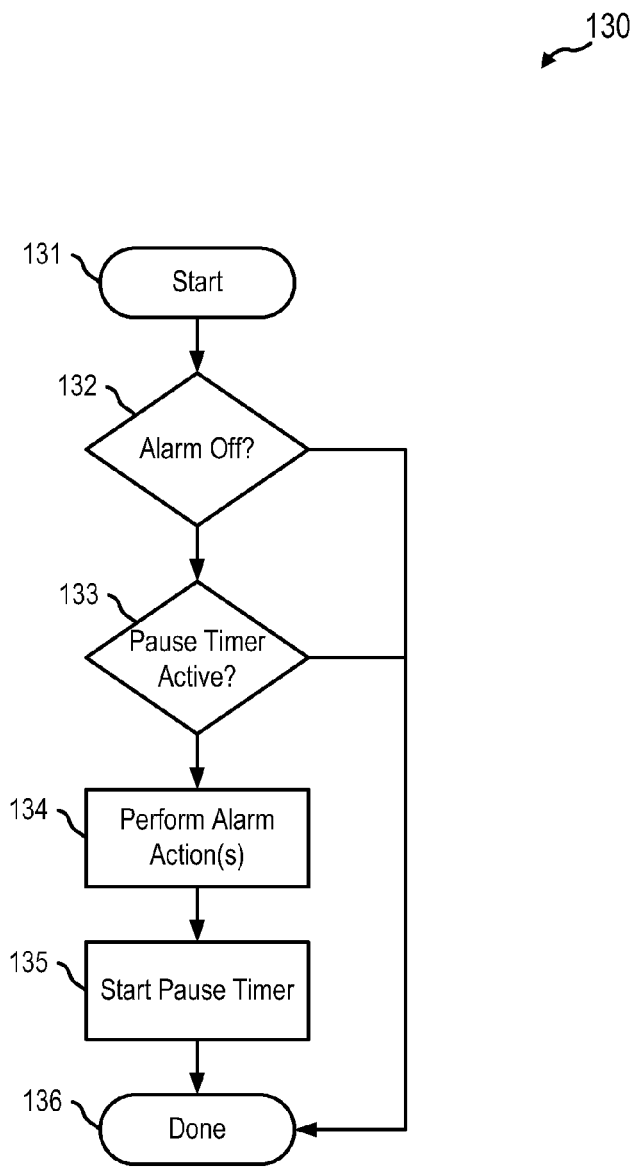
FIG. 10 illustrates a functional block diagram of a method for processing alarm conditions in accordance with various embodiments.

When the Master Alarm signal transitions from OFF to ON, the master alarm processing module 27 may determine and perform an appropriate action in response to the alarm. FIG. 10 illustrates a method 130 for alarm processing in accordance with various embodiments. Method 130 may be performed, for example, by the master alarm processing module 27.

After starting at block 131, the method 130 may check the Alarm Enable signal at block 132. If the Alarm Enable signal is set to FALSE, the method proceeds to Done at block 136. If the Alarm Enable signal is TRUE, the method may check the Pause Timer Active signal at block 133. It the Pause Timer Active signal is TRUE, the method proceeds to Done at block 136. Otherwise, the method triggers the execution of one or more alarm actions at block 134.

Alarm actions may be selected and individually enabled through the graphical user interface described in more detail below. Possible alarm actions include sounding an alarm, turning on a live video display, turning on audio monitoring initiating video, audio, or other sensor recording for later review, sending a text message, sending an email, sending a pager message, sending a message to a secondary monitoring device, recording the event with a time stamp in a database, marking an EEG recording, initiating playback of a pre-recorded video and or audio message, and/or initiating two way communications (intercom) with the monitored location. Finally, the method 130 may start a timer at block 135 before proceeding to Done. The duration of the timer may be the Pause Time specified in the user interface. For the duration of the Pause Time, the Pause Timer Active signal value may be TRUE, after which the value may be FALSE.

In embodiments, the activity monitoring device 5 performs all the tasks detailed in the functional block diagrams. The activity monitoring device 5 also includes a display and means for entering data (the user interface) and performs the Alarm Actions. In the preferred embodiment the activity monitoring device 5 is a smartphone with a touch screen such as an iPhone or Android smartphone, but it can also be a tablet computer, personal computer, or laptop, or any device with similar functionality. In one embodiment, the activity monitoring device is implemented as an application or "App" running on the smartphone operating system. In one embodiment, the sensor system 12 including camera and microphone sensors are implemented as an infra-red, wireless network camera. Communication between the network camera and smartphone may be through wireless Ethernet (Wi-Fi) or some other wired or wireless connection as is known in the art.

In embodiments, the network camera may record on its own and receive control signals from the activity monitoring device 5. For example, the network camera may transmit video to the activity monitoring device 5 at a first resolution but record to a local storage device at a second, higher resolution. This may allow lower resolution video to be transmitted, reducing network bandwidth use and/or power consumption at the activity monitoring device 5 and/or the network camera. The activity monitoring device 5 may communicate with the network camera to control recording of activity events by the network camera. The recorded events (e.g., full-resolution) may be available on the network camera for later viewing (e.g., via the activity monitoring device 5).

Described embodiments include user interface components (e.g., images, video, menus, buttons, etc.) for interacting with display content that is displayed on a display device (e.g., display device 6 of activity monitoring device 5). The interactive display content may be displayed in pages associated with various functions and/or features of various embodiments. As used herein, the term "page" may typically refer to rendered display content while the terms "display" or "screen" may refer to the display content or physical display component depending on context. The "display" or "screen" may be a touch-screen display device allowing interaction with displayed "pages" using touch gestures. In this regard, a "page" may be displayed and/or interacted with by a user via a "display" or "screen."

Typically, the sensors are separate from the activity monitoring device 5, but one or more of the sensors may be included in the device itself. For example, embodiments are directed to using the activity monitoring device 5 as a stand-alone activity monitor system. These embodiments may be implemented as a smartphone and use the on-board sensors of the smartphone (e.g., video camera, microphone, etc.). For example, the activity monitoring device 5 may be used as a stand-alone activity monitor for self-monitoring by patients as described in more detail below.

Figure 11:
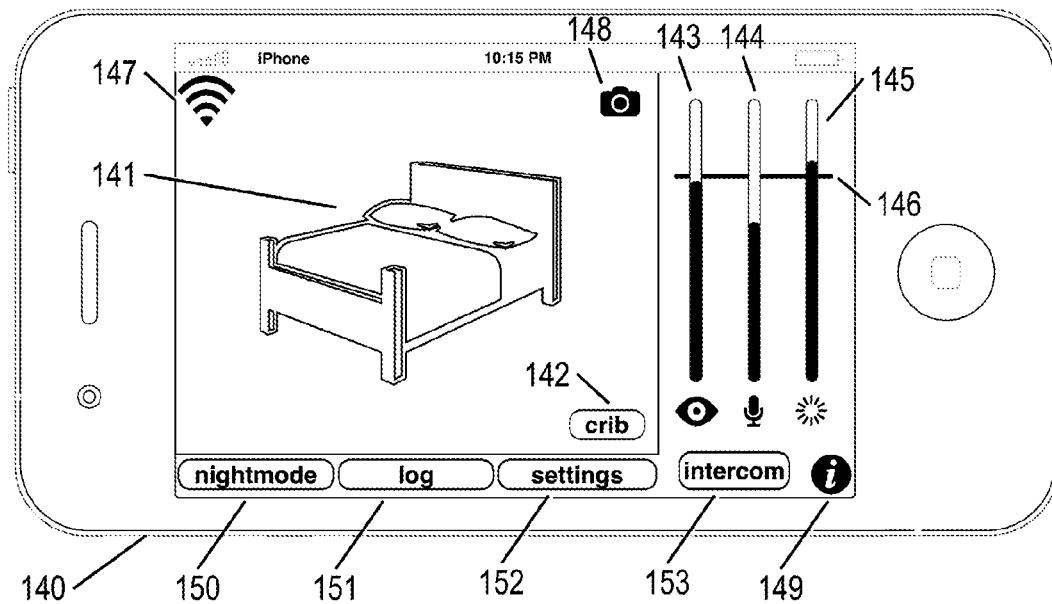
FIG. 11 illustrates a home page of a smartphone based monitoring device application in accordance with various embodiments.

FIG. 11 illustrates a smartphone based monitoring device 140 displaying the home page on its screen. The home page displays the live video image 141 from the video camera in the selected location. Another button (the Location Select button 142) displays the currently selected location, and when touched permits the selection of another location. This button also appears on other pages and performs the same function on all. Touching the intercom 153 will enable two way communications with the monitored location. This can be audio, or audio and video. Also displayed are the Motion Alert Level signal 143, the Audio Meter signal 144, and the Alert Level signal 145 as meters. A line 146 indicates the threshold for the meters, and each of the meters are scaled appropriately so the corresponding threshold is at the line. An icon 147 indicates the state of the sensors. One icon (in the illustration a wave pattern) indicates all sensors are operating correctly. If any sensors are in fault, the icon changes to represent the faulting sensor with a circle and slash overlaid. If multiple sensors are faulty, the icon cycles showing each faulting sensor in sequence. A camera icon 148, when touched, is used to initiate audio and video recording. When this icon is flashing, recording is in process. The information icon 149, when touched, provides version, author, contact, and licensing information.

Figure 12:
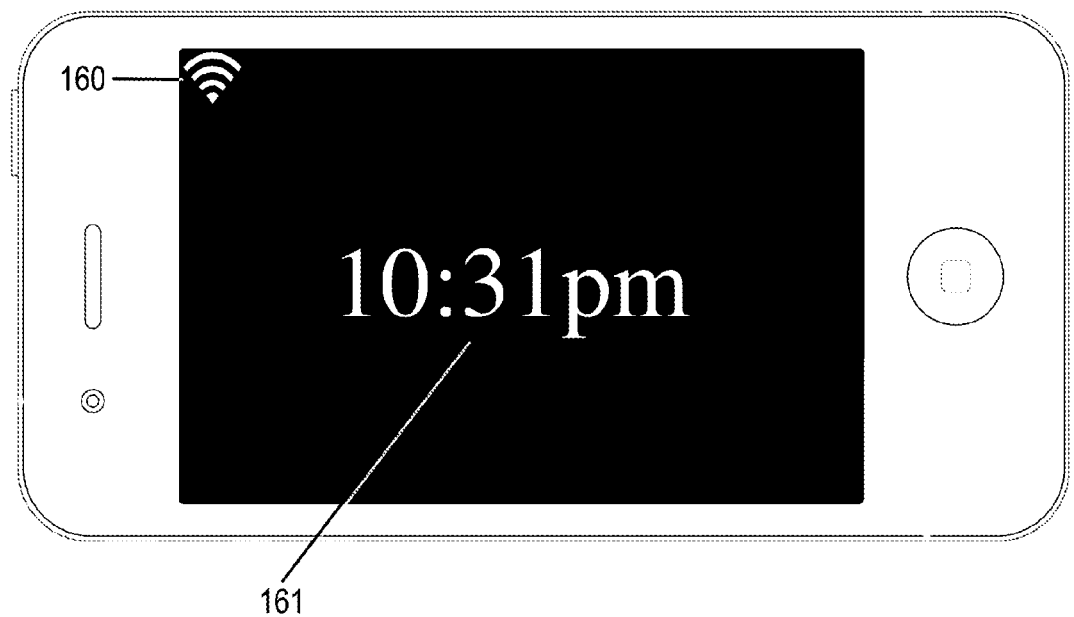
FIG. 12 illustrates a night mode page of a smartphone based monitoring device application in accordance with various embodiments.

The nightmode button 150 changes the display to a simpler, dark display, shown in FIG. 12. In this mode, the only visible item is the sensor status icon 160 and, optionally, a clock 161. Touching anywhere on the screen changes the display back to the home page. In embodiments, the monitoring device 140 includes a "pocket" or "walk-around" mode where the monitoring application is running on the monitoring device 140 but locks the screen so that spurious gestures on the display do not interrupt operation of the monitoring device 140. A specific gesture (e.g., swipe to unlock, etc.) may bring the monitoring device 140 out of the "pocket" mode.

Figure 13:
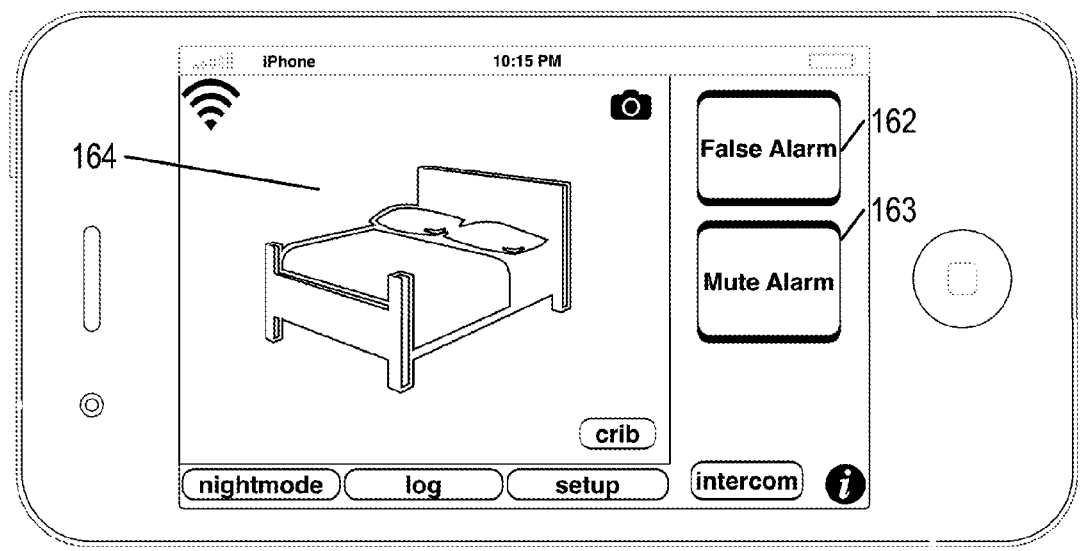
FIG. 13 illustrates an alarm page of a smartphone based monitoring device application in accordance with various embodiments.

If an alarm is triggered while the display is showing either the home page or the nightmode page the display may immediately brighten and switch to the alarm page 164 shown in FIG. 13. The alarm page 164 may be identical to the home page with the exception that the meters are replaced by two large buttons. Touching anywhere on the screen may mute an audible alarm (if it is sounding). Touching False Alarm 162 adds a log entry indicating that the triggered alarm was false, and returns to the page the display was on before the alarm sounded. Touching Mute Alarm 163 simply halts the sounding of the alarm. Touching any other button performs the same function as on the home page.

Figure 14:
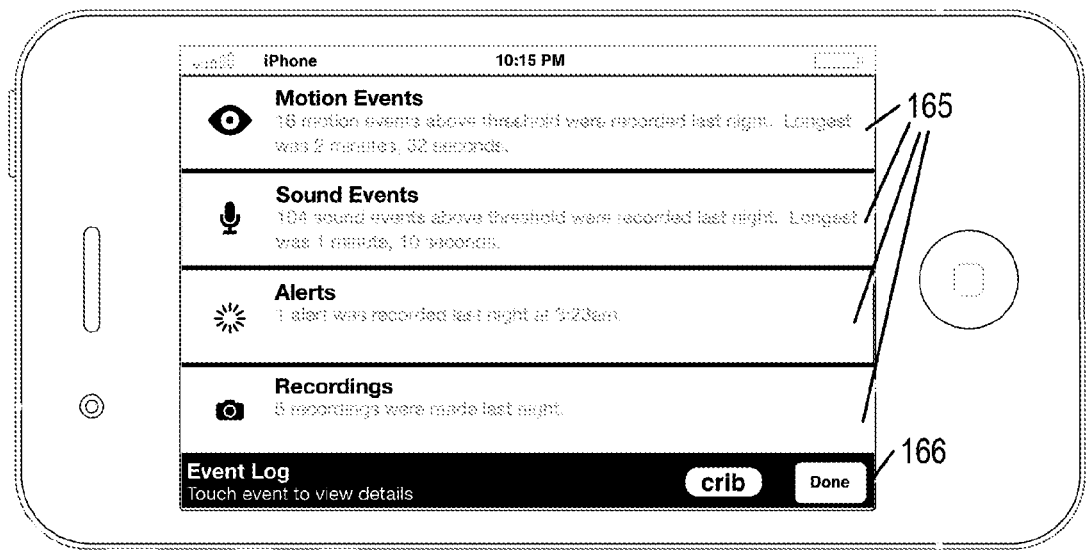
FIG. 14 illustrates a log page of a smartphone based monitoring device application in accordance with various embodiments.

Referring back to the home page shown in FIG. 11, touching the log button 151 changes the display to the log page shown in FIG. 14. The log page provides historical information. Examples of this include the number of motion events over the last 12 hours, the number of alarms, and the number of recordings. Referring to FIG. 14, touching any of the labeled sections 165 will display more detailed information. Touching the Done button 166 returns to the home page.

Figure 22:
FIG. 22 illustrates a motion event log page of a smartphone based monitoring device application in accordance with various embodiments.

Selecting the Motion Events section 165 changes the display to the event log associated with motion events. FIG. 22 illustrates an example of a motion event log page. Each recording 280 may be identified by the recording time 281. As described above, various information may be stored by the activity monitor associated with each event. For example, maximum values of the alert levels (e.g., Motion Alert Level 37, High and Low Audio Alert Levels 47, etc.), triggered alarms, and/or other information may be stored associated with each recording 280. The motion event log page may show some or all of the stored information with each recording 280. For example, the maximum Alert Level (e.g., Motion Alert Level 37), audio level (e.g., High Audio Alert Level 47), and/or duration 282 associated with each recording may be shown. Recordings that happened when an alarm was triggered may be identified by an alarm symbol 283. A thumbnail image 284 of the recording may be shown, and the user may play the video associated with the recording 280 by touching the thumbnail.

Figure 15:
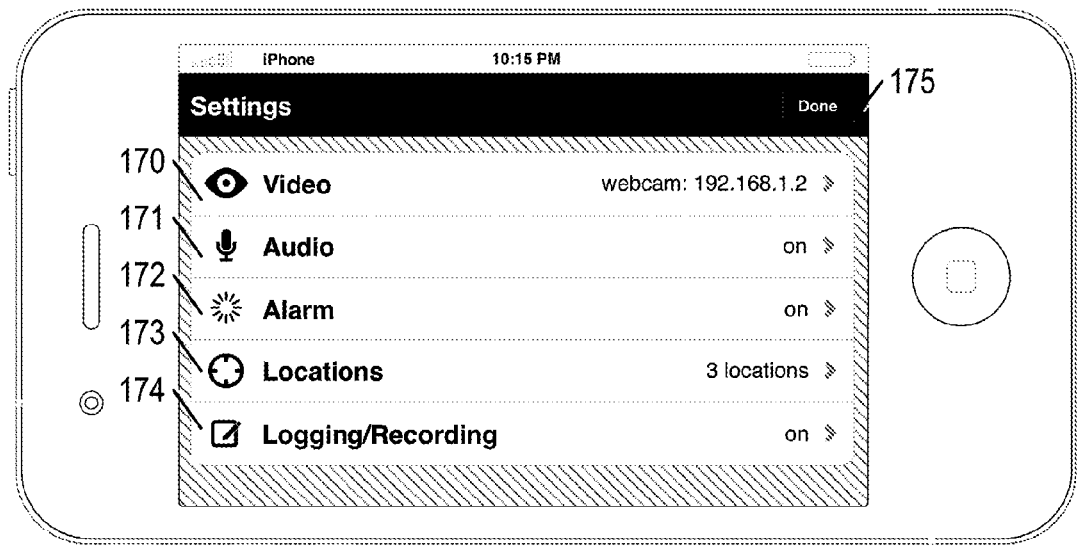
FIG. 15 illustrates a settings home page of a smartphone based monitoring device application in accordance with various embodiments.

Referring again to FIG. 11, touching the settings button 152 on the home page changes the display to the Settings home page shown in FIG. 15. Touching Video 170 changes the page to the Video Settings page shown in FIG. 16. Touching Audio 171 changes the page to the Audio Settings page shown in FIG. 18. Touching Alarm 172 changes the page to the Alarm Settings page shown in FIG. 19. Touching Locations 173 changes the page to the Location Settings page shown in FIG. 20. Touching Logging/Recording 174 changes the page to the Logging/Recording Settings page shown in FIG. 21. Selecting by touching on a labeled row changes the display to that settings page. Touching Done 175 returns to the home page. Note that if additional sensors are available, new entries would be added here for their associated settings pages.

Figure 16:
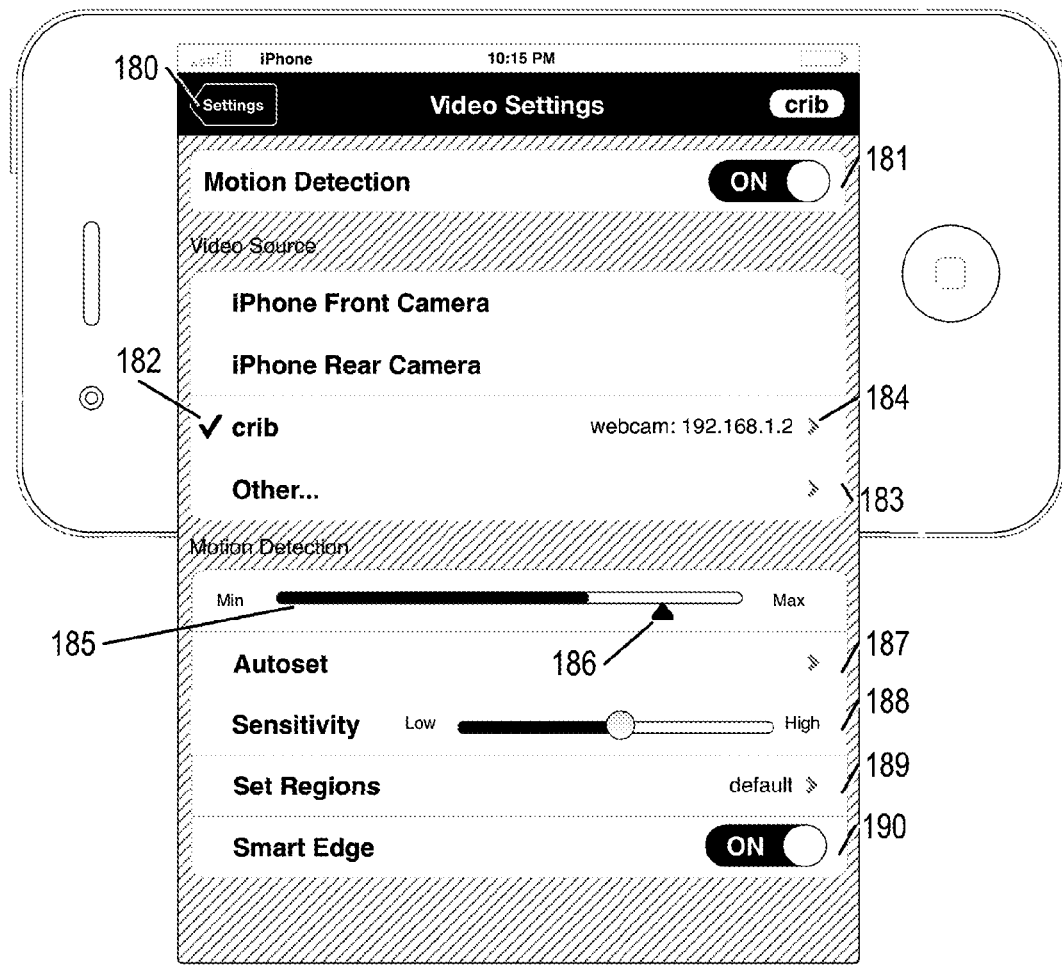
FIG. 16 illustrates a video settings page of a smartphone based monitoring device application in accordance with various embodiments.

Referring to FIG. 16, the Video Settings page is used to configure the behavior of the video sensor (e.g., camera 13, etc.) and associated processing. Touching the Settings button 180 changes the page back to the Settings Page shown in FIG. 15. This button appears on multiple pages and performs the same action on all. Note that even though the settings page shown in FIG. 16 extends beyond the display area in this illustration, it is actually displayed as a scrollable table contained within the display area. First is a Motion Detection on-off switch 181. When off, all video motion detection, display, and alert/alarm is disabled. The next group is used to select the source for the video. A check mark 182 indicates the currently selected source. New sources may be added by selecting "Other . . ." 183. Touching the arrow 184 on sources requiring configuration changes to a page where details for that source may be entered. Details include items such as camera brand, camera IP address, etc. The next section is used to configure the motion detection settings. A meter 185 is indicating the current Motion Level. A marker 186 may be moved by dragging it left and right with a finger to set the Motion Threshold 82. Touching Autoset 187 changes to a page that can automatically set the Motion Threshold 82. The user presses this when no motion of interest is present. The Motion Threshold 82 is then automatically adjusted to a level slightly higher than the current Motion Level. A more sophisticated implementation can also automatically add an Exclude Region in areas of the image that have high motion. This will exclude areas with motion that is not of interest.

Sensitivity 188 allows the user to set the Motion Alarm Threshold. High sensitivity results in faster response, but more false alarms. Low sensitivity results in slower response, but reduces the number of false alarms.

Figure 17:
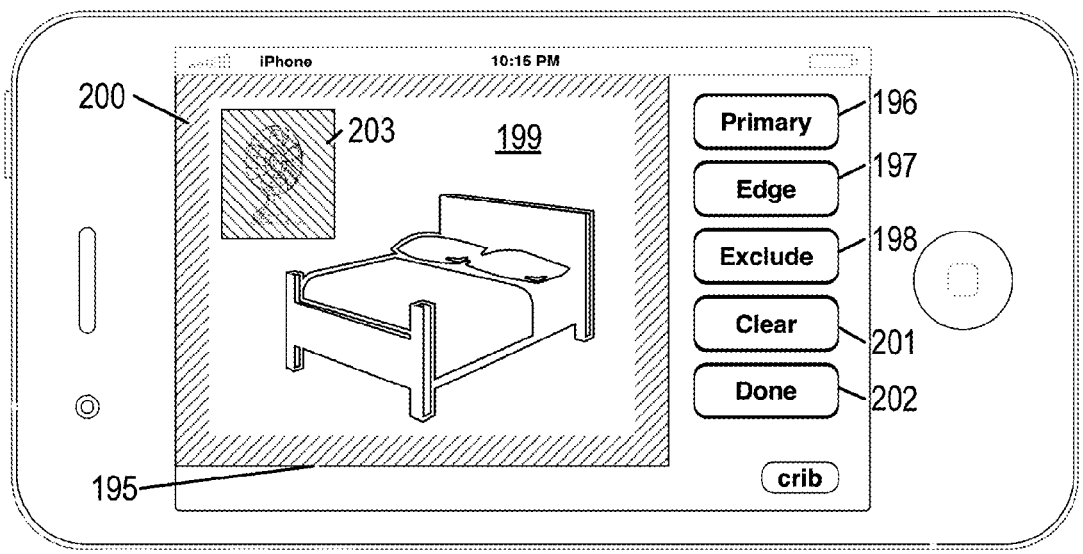
FIG. 17 illustrates a region settings page of a smartphone based monitoring device application in accordance with various embodiments.

Set Regions 189 changes the display to the region settings page shown in FIG. 17. This page displays a live view 195 from the video source. The Primary 196, Edge 197, and Exclude 198 buttons are used to modify the Primary Region 199 and/or Edge Region 200 for use by the motion alert integrator. Initially, the Primary Region may encompass the entire image. By touching Edge 97, one can then "paint" the image with a finger. Painted areas are indicated by an overlaid, transparent color. By dragging a finger around the perimeter of the image, the Edge Region 200 may be defined. While the Edge Region 200 is being modified, the Primary Region 199 may be modified to exclude the area included in the Edge Region 200. Touching Primary 196 may clear the painted area, expanding the Primary Region 199 and reducing the Edge Region 200. Note that the extent of the regions is arbitrary and not limited in location. Touching Exclude 98 may allow the user to paint areas 203 that are excluded from both the Primary Region 199 and Edge Region 200. These areas are shown in a different transparent color. By touching Primary 196 or Edge 197 one can then paint over the exclude area, reducing or even eliminating it. Touching Clear 201 resets the regions to their initial state and clears the exclude area(s). Touching Done 202 returns the display to the Video Settings Page.

Returning to FIG. 16, the smart edge switch 190 turns on the multi-region processing performed by the motion alert integrator 36 as discussed above. In some embodiments, other multi-region processing options include multi-region behavior, region weighting and/or enabling other sensors to be included as regions in multi-region processing, as described above.

Figure 18:
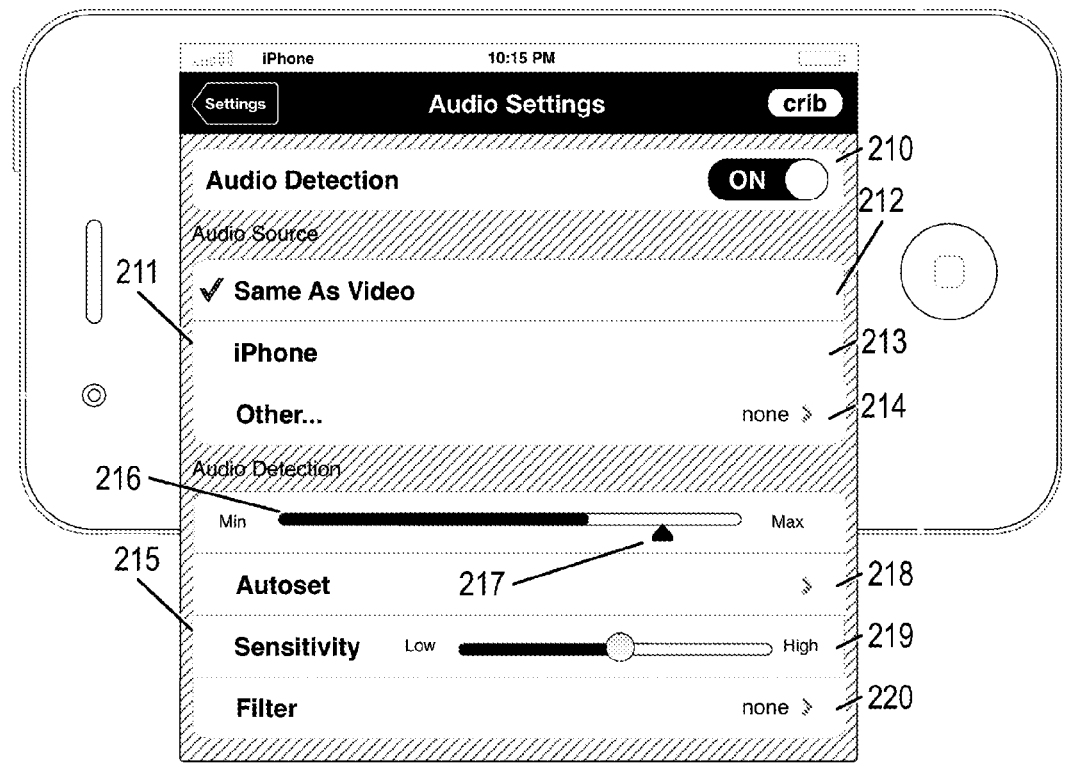
FIG. 18 illustrates an audio settings page of a smartphone based monitoring device application in accordance with various embodiments.

Referring back to FIG. 15, touching Audio 171 on the Settings page changes the display to the Audio Settings page shown in FIG. 18. Like the Video Settings page, there is a switch 210 to enable or disable the audio level detection. The next section 211 is used to specify the audio sensor source. Selecting Same As Video 212 will cause the audio to come from the microphone associated with the video source specified on the Video Settings page. The iPhone choice 213 selects the built-in microphone in the smartphone. Other 214 changes the display to a page where one can specify another source, such as a wireless IP microphone.

The Audio Detection section 215 is used to configure the audio detection settings. For example, a meter 216 may show the Audio Meter signal. A marker 217 may be moved to set the High Audio Alert Threshold. Touching Autoset 218 changes to a page that can automatically set the High Audio Alert Threshold. The user presses this when no sound of interest is present. The threshold may then be automatically adjusted to a level slightly higher than the current Audio Meter value. A more sophisticated implementation can also automatically add filters to detect and exclude background noise. Sensitivity 219 allows the user to set the High Audio Alert Threshold. High sensitivity results in faster response, but more false alarms. Low sensitivity results in slower response, but reduces the number of false alarms. Touching Filter 220 changes the display to a page that enables setting various optional audio filters as implemented in the Audio Sensor Processor. If the Low Audio Alert is implemented, then additional controls are added to this page to independently configure it like the High Audio Alert.

Figure 19:
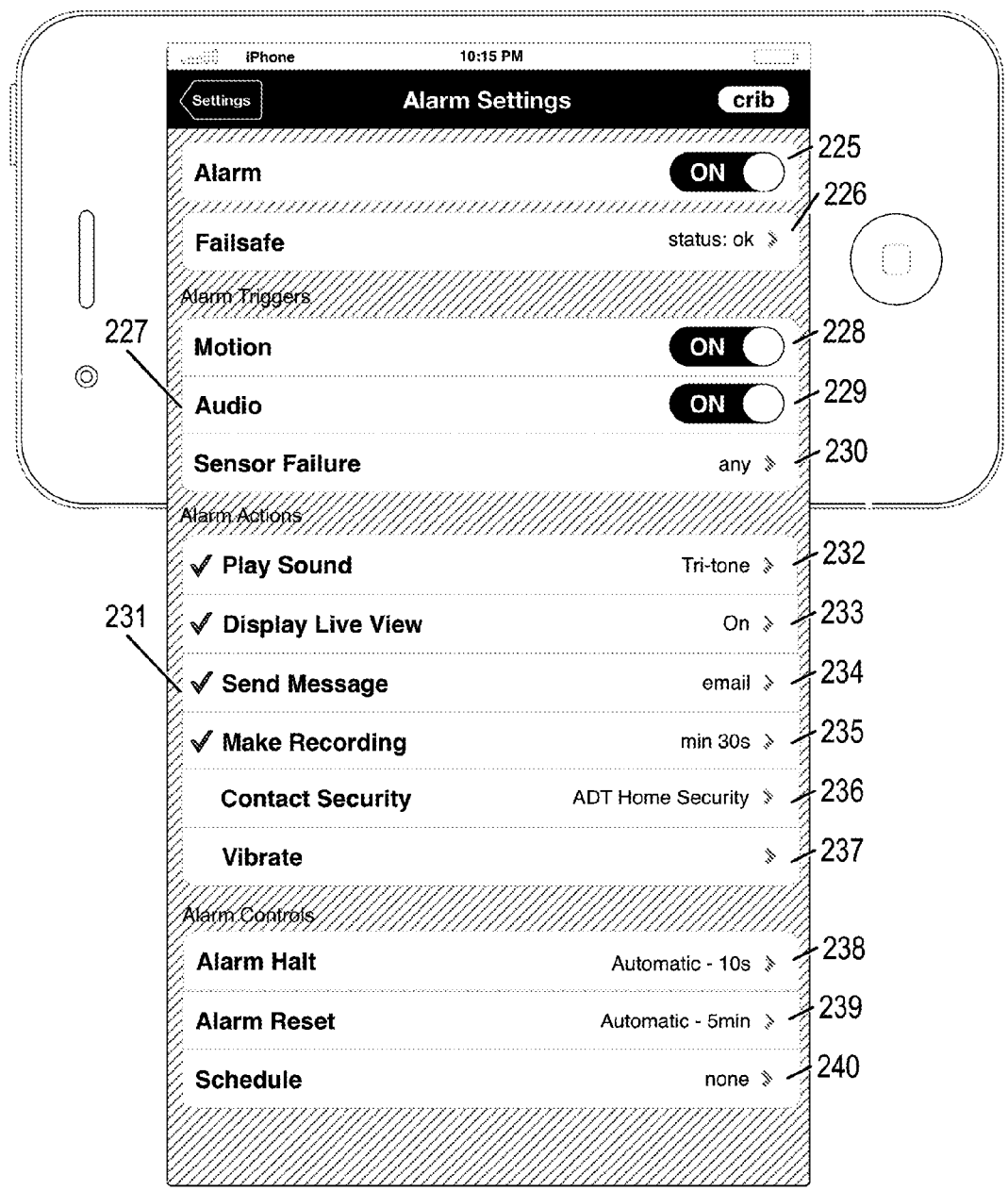
FIG. 19 illustrates an alarm settings page of a smartphone based monitoring device application in accordance with various embodiments.

Returning to FIG. 15, touching Alarm 172 changes the display to the Alarm Settings page illustrated in FIG. 19. The Alarm switch 225 is a master switch that may enable or disable all alarm processing. Touching Failsafe 226 changes to a page for configuring the Failsafe function. The failsafe function provides a means to alert the user if the monitoring device is not functioning properly. It may have a hardware problem, or it may simply be switched off. In the case where the monitoring device is a smartphone running an application, the user may have failed to start the application. If the failsafe function is enabled, the monitoring device may periodically communicate with another device (the Failsafe Monitor). The Failsafe monitor is always running, in the preferred embodiment it is a server located at a distant location, connected by the Internet to the Monitor Device. If the Failsafe Monitor fails to communicate with the monitoring device for a selectable period of time, it can send a message to the user. The message could be a text message, phone call, email, or some other means that does not require a functioning monitoring device. The failsafe settings page includes settings for establishing contact with the Failsafe Monitor such as a username and password. It also includes settings to specify the means of notification, how fast to report faults, and whether to only alert during specified times.

The next section 227 in FIG. 19 allows one to configure the behavior of the alarm/alert processor. The Motion Detector 228 and Audio Detector 229 switches duplicate and mirror the function of switch 181 in FIG. 15 and switch 210 in FIG. 18, respectively. Touching Sensor Failure 230 changes the display to a sensor failure settings page. Here, one can select which sensors, or which combination of sensors, should trigger an Alarm.

The Alarm Actions section 231 on FIG. 19 is used to select what happens when an alarm is triggered. Each of the individual options has a corresponding settings page. The Alarm Action Play Sound 232 may play a selected sound from the speaker in the monitoring device. Options may include, for example, picking the particular sound to be played, and sound level. Display Live View 233 enables or disables the live video on the home page (141 on FIG. 11) and the alarm page (164 on FIG. 13). This is useful in cases where for privacy reasons live video access is restricted, but the video is still being used for motion detection. Send Message 234 enables an alarm to send a message to another device, such as a text message, email, or automated phone call. This can also be set to only send a message if the alarm is not acknowledged on the alarm page for a defined period of time. Make Recording 235 enables automatic recording of the sensors on an alarm. Touching this changes the display to the Logging/Recording Settings page shown in FIG. 21. Contact Security 236 enables an alarm monitoring company to be notified on an Alarm. Settings specify the particular company, and configure the interface to the alarm company's equipment. Vibrate 237 simply activates the smartphone vibrate function, the vibration pattern may be specified. Other possible alarm actions include turning on the intercom, and/or playing a pre-recorded audio and/or video message in the monitored location.

The Alarm Halt 238 control specifies how an alarm, once triggered, is ended. Options are manual, which requires the user to acknowledge the alarm, or automatic, which will halt the alarm a fixed period of time after it is triggered (the alarm may still be manually halted sooner). The Alarm Reset 239 is used to control how long the alarm is disabled after an alarm has been triggered and ended. Options are manual, meaning that after an alarm the alarm is turned off using the Alarm Master Switch, or automatic which will re-enable the alarm in the specified time. This time may be the Pause Time used by the Alarm Processor.

Schedule 240 is used to define periods during which the alarm is disabled. For example, it may be useful to disable the alarm during daytime to prevent false alarms. The schedule may be specified on a repeating, weekly basis, with multiple start and stop times during the day.

Figure 20:
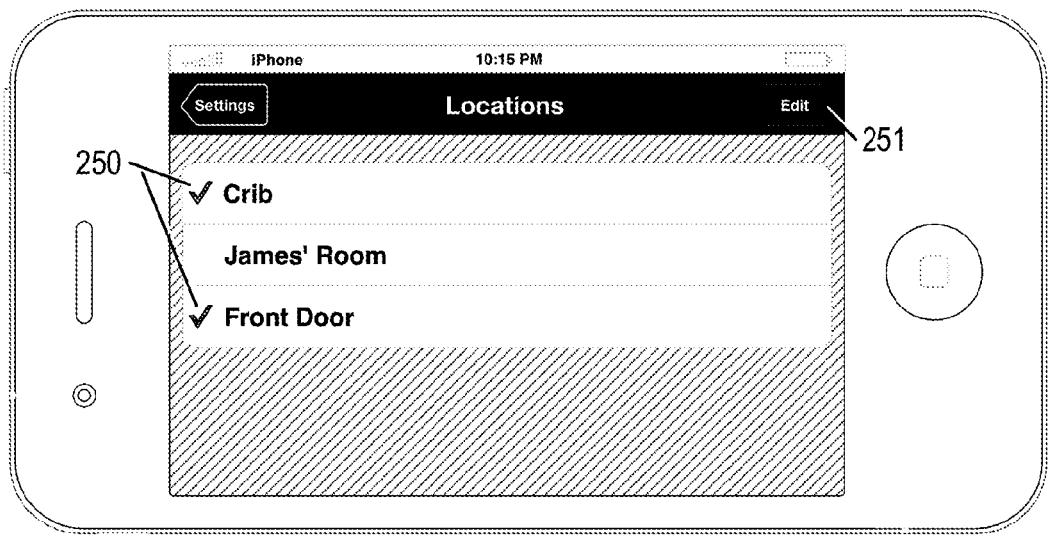
FIG. 20 illustrates a location settings page of a smartphone based monitoring device application in accordance with various embodiments.

Returning to FIG. 15, touching Locations 173 changes the display to the Locations Settings page illustrated in FIG. 20. This page is used to create and select locations to be monitored. Currently monitored locations may be indicated by a check mark 250. Touching Edit 251 permits creating and deleting locations. These locations are selected using the Location Select button (see 142 on FIG. 11 for an example) that appears on multiple pages.

Figure 21:
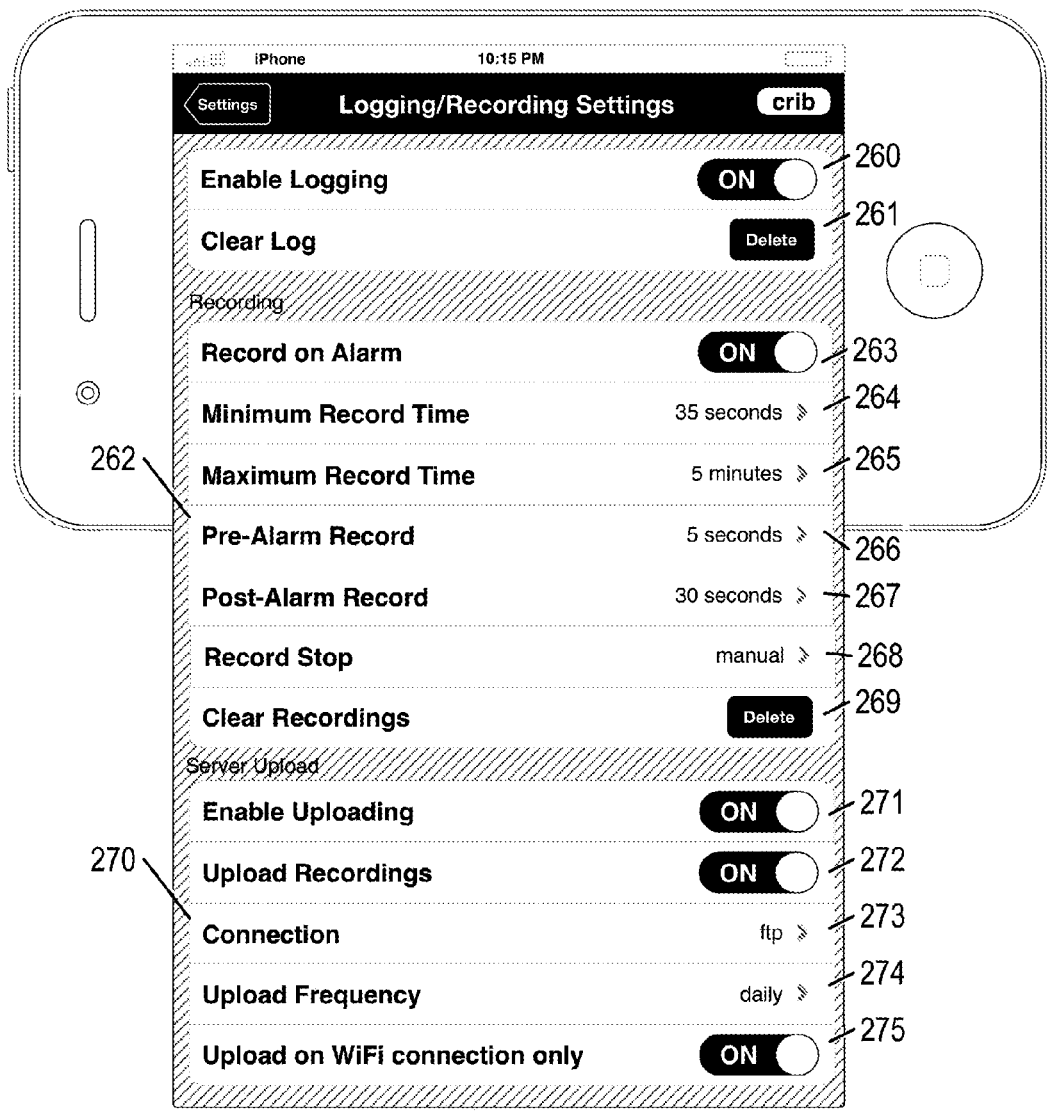
FIG. 21 illustrates a logging/recording settings screen of a smartphone based monitoring device application in accordance with various embodiments.

Returning to FIG. 15, touching Logging/Recording 174 changes the display to the Logging/Recording Settings page illustrated in FIG. 21. This page is used to control the logging of events and the recording of data. The first switch 260 enables and disables logging of data. The next switch 261 simply clears all data from the log.

In the recording section 262, the Record On Alarm switch 263 mirrors the action of the Make Recording 235 switch in FIG. 19. The minimum 264 and maximum 265 recording length may also be specified, as well as a "pre-alarm" 266 time and "post-alarm" 267 time (e.g., corresponding to time periods 113 and 115 of FIG. 8, respectively). Record Stop 268 specifies when recording is stopped. Recording may be set to stop on alarm acknowledgement, or to continue as long as the Alert Level is above threshold (Variable Alert), or for a fixed period of time, or until the user manually stops it. Note that the maximum recording length overrides this setting. For example, if pre-alarm time is set to 15 seconds, the post-alarm time is set to 30 seconds, and the recording stop is set to Variable Alert, and the Alert Level is above threshold for 45 seconds, the total recording length will be 15+45+30 or 90 seconds long. If the Alert Level is above threshold for 4 minutes and 45 seconds, however, the maximum recording length 265 will limit the total recording length to 5 minutes. Touching the delete button 269 clears all recordings from memory. Typically the monitoring device is recording all the sensors all the time into a buffer. When a recording is saved the pre-alarm data is retrieved from the buffer.

The Server Upload section 270 is used to specify what is done with the log data and recordings. Uploading may be individually enabled and disabled for log files 271 and recordings 272. Connection 273 is used to specify how and to where the data is transferred. FTP, network file sharing, and other "cloud" computing options are available. Upload Frequency 274 specifies how often the data is transferred, and Upload on Wi-Fi connection only 275 is used to optionally prevent large amounts of data over more expensive wireless connections.

Following are several examples of implementations of various embodiments of the invention, and possible applications.

One useful implementation is to use a smartphone or tablet as the monitoring sensors (e.g., sensor system 12). For example, two identical smartphones may be configured such that one does the monitoring and the other does the sensing. This is convenient for travel where a parent may want to monitor and communicate with a child staying in another room. They can even both be performing both actions, each location monitoring the other. This can also be implemented on a tablet computer, personal computer, or a custom, purpose built device.

Another implementation of the monitoring device is on a computer which can simultaneously monitor and display video and activity from multiple locations at once. A hospital ward or other patient care facility can use this to monitor multiple patients from one location.

The multiple region processing of the video can be used to handle other scenarios. For example, elderly persons could be monitored by looking for motion in the Primary Region followed by motion in the Edge Region that may indicate that someone has left a location. An alarm could be triggered if the person does not return in a preset period of time.

If the motion processing frame rate high enough, more sophisticated motion can be detected. For example, a rhythmic motion may indicate a seizure that should trigger an alarm.

In embodiments, an infra-red video camera is used for motion detection, providing an image under both lit and dark conditions. A characteristic of the image provided under dark conditions using an infra-red camera is that it is monochrome. The absence of color in the images can be used by the monitoring device to detect if the monitored location is dark. This can then be used to only enable alarms when the monitored location is dark. In the case where the subject needs to be monitored only in sleep this feature prevents false alarms and removes the need to manually or through a schedule turn the alarm on and off.

It is useful in some cases to have two alarms, one that is triggered before the other. This can be done by having two different Alert Level Thresholds, one higher than the other. Different actions then can take place, one before the other. A useful application of this is in a baby monitor. Motion or noise from the baby can trigger an entertaining or soothing action in the crib in an attempt to settle the baby. For example, a video of the mother making soothing gestures and noises may be played back. This may be sufficient to help the baby go back to sleep without intervention from a parent. If this fails, and the motion/sound continues, the parent can then be notified through the secondary alarm.

In the case of monitoring an epilepsy patient, seizures or sudden unexplained death in epilepsy (SUDEP) at night are a concern. Close monitoring is often called for. This invention can monitor several different sensors and provide assistance in alerting caregivers. A minimal configuration with just a video camera looking for motion as described above is very effective. Adding a heart rate sensor can improve performance as it is common for a patients heart rate to increase during a seizure. A breathing sensor can help alert a caregiver to a seizure or the possible initiation of a SUDEP event. In this case, the seizure monitor receives the breath rate data, compares it against a low threshold, and then performs the selected alarm actions if it drops below the threshold. All the sensor data can be recorded and timestamped for later analysis. This can be helpful in diagnosing seizures.

Some epilepsy patients have seizures at night and may not be aware that they occur. For these patients, having multiple seizures during the night may be a significant concern. Alerting an epilepsy patient after a seizure may help the patient to prevent further seizures (e.g., by taking medicine, etc.). As described above, the activity monitoring device 5 (e.g., implemented in a smartphone, etc.) may be used as a stand-alone activity monitoring system 10 for self monitoring of a patient. The smartphone may be set up to monitor the patient at night with the alarm set to continually sound upon detecting an event until manually shut off. While an epileptic patient may be unresponsive for some period of time after a seizure, when the patient does become responsive they will be alerted by the alarm that an event may have occurred and can review the event to determine if they should take action to prevent future seizures.

Although the previous descriptions have focused on monitoring the health and safety of people, this invention is not limited to those applications. Monitoring pets and machinery is also facilitated by this invention.

Figure 23:
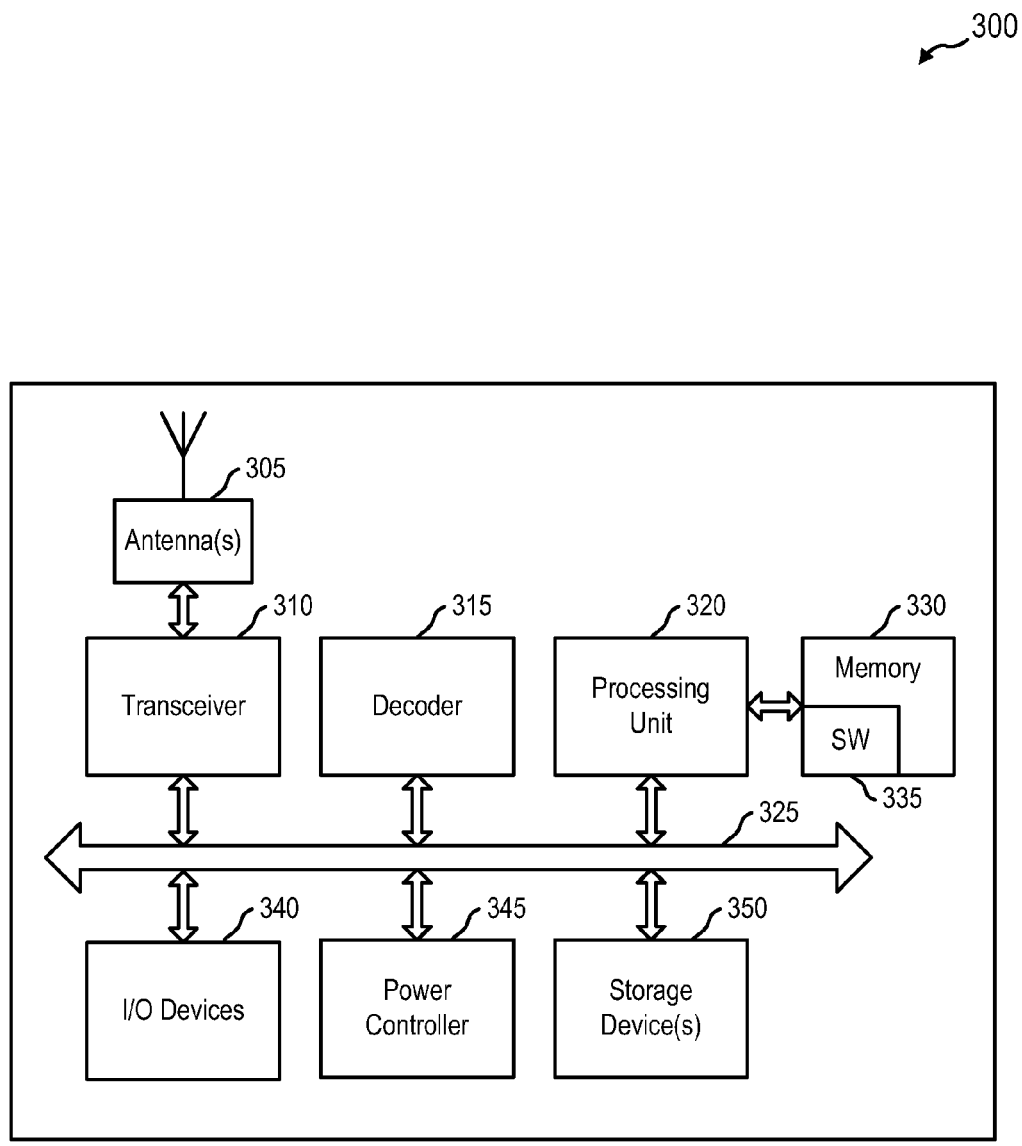
FIG. 23 is a block diagram illustrating an example of a device for activity monitoring in accordance with various embodiments.

FIG. 23 is a block diagram illustrating an example of a device 300 for activity monitoring in accordance with various embodiments. Device 300 may illustrate, for example, aspects of activity monitoring device 5 illustrated in FIG. 1. Device 300 includes antenna(s) 305, transceiver 310, decoder 315, processing unit 320, memory 330, I/O devices 340, power controller 345, and storage device(s) 350. The various components of the device 300 may be coupled together by a bus system 325 which may include a power bus, a control signal bus, and a status signal bus in addition to a data bus. For the sake of clarity, the various busses are illustrated in FIG. 22 as the bus system 325. The antenna(s) 305 and transceiver 310 may allow transmission and reception of data, such as video and/or audio communications, between the device 300 and one or more external device such as a sensor system and/or network. The transceiver 310 may also interface to various wired connections that permit data to be exchanged with other devices. Device 300 may be, for example, a smartphone, tablet, and/or other computing device.

The I/O devices 340 may include one or more display devices and/or user input devices. For example, I/O devices 340 may include a display, keyboard, mouse, clickwheel, scrollwheel, touchscreen, buttons, and/or other I/O devices for user input and/or information output.

The processing unit 320 may control operation of the device 300. The processing unit 320 may also be referred to as a central processing unit (CPU). The processing unit 320 may be configured to receive data from a sensor system (e.g., sensor system 12), process the data to detect "interesting" activity events, and perform actions based on detecting the events. The processing unit 320 may detect activity events based on video processing of a substantially live sequence of images received from a video camera. The processing unit 320 may detect events based on other sensors and may use a combination of sensor data to detect events. The processing unit 320 may store event data (e.g., using storage device(s) 350) from the one or more sensors (e.g., video, audio, etc.) for interesting events and/or trigger an alarm action. Alarm actions may include sounding an audible alarm and enabling a substantially live video display concurrently with the audible alarm (e.g., via I/O devices 340).

The processing unit 320 may use video processing techniques such as the motion estimation and multi-region processing described above to detect events. Event detection may include integrating motion levels from one or more regions to determine a motion alert level. Comparing the motion alert level with one or more thresholds may trigger various actions such as recording the event and/or performing an alarm action. Multi-region processing may include applying coefficients to motion levels from one or more regions to generate the motion alert level. The thresholds may be used to suppress or enhance motion detection in one region based on motion in one or more regions, motion transitions, and/or motion entry and/or exit points. The processing unit 320 may use other sensor information such as an audio signal to detect events. One or more of these operations may be performed by decoder 315 in cooperation with processing unit 320.

The memory 330 may include read-only memory (ROM) and random access memory (RAM). A portion of the memory 330 may also include non-volatile random access memory (NVRAM). The memory 330 provides instructions and data to the processing unit 320. The steps of the methods discussed above may also be stored as instructions in the form of software and/or firmware 335 located in the memory 330. These instructions may be executed by the processing unit 320 of the device 300. The software and/or firmware 335 may also include additional software elements, including an operating system and/or other code, such as programs or applications designed to implement methods of the invention.

The storage device(s) 350 may be a computer-readable storage media or storage media reader connected to any machine-readable storage medium, the combination comprehensively representing remote, local, fixed, or removable storage devices or storage media for temporarily or more permanently containing computer-readable information. The steps of the methods discussed above may also be stored as instructions in the form of software and/or firmware on storage device(s) 350 and may be loaded from storage device(s) 350 into memory 330 as software and/or firmware 335. It will be apparent to those skilled in the art that substantial variations may be used in accordance with specific requirements. For example, customized hardware might also be used, or particular elements might be implemented in hardware, software (including portable and/or cloud-based software), or both.

It should be noted that the methods, systems and devices discussed above are intended merely to be examples. It must be stressed that various embodiments may omit, substitute, or add various procedures or components as appropriate. For instance, it should be appreciated that, in alternative embodiments, the methods may be performed in an order different from that described, and that various steps may be added, omitted or combined. Also, features described with respect to certain embodiments may be combined in various other embodiments. Different aspects and elements of the embodiments may be combined in a similar manner. Also, it should be emphasized that technology evolves and, thus, many of the elements are exemplary in nature and should not be interpreted to limit the scope of the invention.

Specific details are given in the description to provide a thorough understanding of the embodiments. However, it will be understood by one of ordinary skill in the art that the embodiments may be practiced without these specific details. For example, well-known circuits, processes, algorithms, structures, and techniques have been shown without unnecessary detail in order to avoid obscuring the embodiments.

Also, it is noted that the embodiments may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure.

Moreover, as disclosed herein, the term "memory" or "memory unit" may represent one or more devices for storing data, including read-only memory (ROM), random access memory (RAM), magnetic RAM, core memory, magnetic disk storage mediums, optical storage mediums, flash memory devices or other computer-readable mediums for storing information. The term "computer-readable medium" includes, but is not limited to, portable or fixed storage devices, optical storage devices, wireless channels, a sim card, other smart cards, and various other mediums capable of storing, containing or carrying instructions or data.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a computer-readable medium such as a storage medium. Processors may perform the necessary tasks.

Having described several embodiments, it will be recognized by those of skill in the art that various modifications, alternative constructions, and equivalents may be used without departing from the spirit of the invention. For example, the above elements may merely be a component of a larger system, wherein other rules may take precedence over or otherwise modify the application of the invention. Also, a number of steps may be undertaken before, during, or after the above elements are considered. Accordingly, the above description should not be taken as limiting the scope of the invention.

What is claimed is:

1. A system for monitoring a patient, comprising:
a video camera that captures images of a patient location;
a video processing device coupled with the video camera, the video processing device configured to:
receive a substantially live sequence of the captured images;
compare each image of the sequence of images with one or more preceding images to determine a sequence of motion levels associated with the sequence of images, each motion level of the sequence of motion levels representing an amount of change for at least one region of the each image relative to the at least one region of the one or more preceding images;
compare the sequence of motion levels associated with the sequence of images to a motion threshold;
determine a motion alert level signal based on the comparison by increasing the motion alert level signal responsive to determining that a first one or more motion levels of the sequence of motion levels exceeds the motion threshold and decreasing the motion alert level signal responsive to determining that a second one or more motion levels of the sequence of motion levels is less than the motion threshold;
compare the motion alert level signal with a motion alarm threshold; and
generate a motion alarm signal based at least in part on determining that the motion alert level signal exceeds the motion alarm threshold.

2. The system for monitoring a patient of claim 1, further comprising:
a video display device coupled with the video camera; and
an alarm processor coupled with the motion alarm signal, the alarm processor configured to:
trigger an audible alarm based at least in part on the motion alarm signal; and
enable, concurrently with the audible alarm, a substantially live display of the sequence of images on the video display device.

3. The system for monitoring a patient of claim 1, further comprising:
a microphone that captures an audio signal from the patient location; and
an audio detector coupled with the microphone, the audio detector configured to:
receive the audio signal; and
determine an audio meter signal based at least in part on the received audio signal; and
an audio alert integrator configured to:
determine an audio level signal based at least in part on an integrating function of a plurality of values of the audio meter signal;
compare the audio level signal with an audio alarm threshold; and
generate an audio alarm signal responsive to detecting that the audio level signal exceeds the audio alarm threshold.

4. The system for monitoring a patient of claim 3, wherein determining the audio level signal comprises:
comparing the plurality of values of the audio meter signal to a high audio threshold;
increasing the audio level signal based on values of the audio meter signal that exceed the high audio threshold; and decreasing the audio level signal based on values of the audio meter signal that do not exceed the high audio threshold.

5. The system for monitoring a patient of claim 3, wherein the audio alert integrator is further configured to:
compare the plurality of audio values of the audio meter signal to a low audio threshold to produce a low audio detection signal;
determine a low audio level signal based at least in part on the low audio detection signal;
compare the low audio level signal with a low audio alarm threshold; and
generate a low audio alarm signal responsive to detecting that the low audio level signal exceeds the low audio alarm threshold.

6. The system for monitoring a patient of claim 3, further comprising:
an alarm processor coupled with the motion alarm signal and the audio alarm signal, the alarm processor configured to:
trigger an alarm action based on one or more of the motion alarm signal and the audio alarm signal.

7. A method for monitoring a patient, comprising:
receiving a substantially live sequence of images of a patient location;
comparing each image of the sequence of images with one or more preceding images to determine a sequence of motion levels associated with the sequence of images, each motion level of the sequence of motion levels representing an amount of change for at least one region of the each image relative to the at least one region of the one or more preceding images;
comparing the sequence of motion levels associated with the sequence of images to a motion threshold;
determining a motion alert level signal based on the comparison by increasing the motion alert level signal responsive to determining that a first one or more motion levels of the sequence of motion levels exceeds the motion threshold and decreasing the motion alert level signal responsive to determining that a second one or more motion levels of the sequence of motion levels is less than the motion threshold;
comparing the motion alert level signal with a motion alarm threshold; and
generating a motion alarm signal based at least in part on detecting that the motion alert level signal exceeds the motion alarm threshold.

8. The method of claim 7, further comprising:
triggering an audible alarm at a monitoring device based on the motion alarm signal; and
enabling a substantially live display of the sequence of images on a display device of the monitoring device concurrently with the audible alarm.

9. The method of claim 7, further comprising:
initiating bidirectional audio communication between the patient and a monitoring device based on the motion alarm signal.

10. The method of claim 7, wherein the comparing of each image of the sequence of images with one or more preceding images comprises:
comparing a first region of each image of the sequence of images with the first region of the one or more preceding images to generate a first sequence of motion levels associated with the first region for the sequence of images; and
comparing a second region of each image of the sequence of images with the second region of the one or more preceding images to generate a second sequence of motion levels associated with the second region for the sequence of images,
and wherein comparing the sequence of motion levels comprises:
comparing the first sequence of motion levels to a first threshold to generate a first motion detection signal associated with the first region; and
comparing the second sequence of motion levels to the first threshold to produce a second motion detection signal associated with the second region.

11. The method of claim 10, wherein determining the motion alert level signal comprises:
applying a first weighting coefficient to the first motion detection signal;
applying a second weighting coefficient to the second motion detection signal; and
determining the motion alert level signal based at least in part on the weighted first motion detection signal and the weighted second motion detection signal.

12. The method of claim 10, further comprising:
determining, for a motion event of the patient based on the comparing of the first and second regions, a region transition from the first region to the second region; and
suppressing triggering of alarm actions based on the motion alarm signal for a predetermined time period based on the region transition for the motion event.

13. The method of claim 10, wherein the first region comprises a center region and the second region comprises an edge region.

14. The method of claim 10, further comprising:
receiving user input identifying a first portion of a display screen; and
determining one of the first region or the second region based at least in part on the received user input.

15. The method of claim 14, wherein receiving the user input comprises:
enabling a substantially live display of the sequence of images on the display device; and
receiving user input corresponding to a selection of the first portion of the display screen.

16. The method of claim 7, further comprising:
comparing the motion alert level signal with a motion event threshold; and
storing, responsive to the motion alert level signal exceeding the motion event threshold, a time period of the sequence of images.

17. The method of claim 16, wherein the time period is based at least in part on an elapsed time of the motion alert level signal exceeding the motion event threshold.

18. The method of claim 16, wherein storing the time period of the sequence of images comprises storing a predetermined time period of the sequence of images received prior to the motion level signal exceeding the motion event threshold.

19. The method of claim 16, further comprising:
associating a value of the motion level signal with each stored time period of the sequence of images; and
displaying a stored event list, wherein each stored event of the stored event list comprises a stored time period of the sequence of images and the associated motion level signal value.

20. The method of claim 16, wherein the motion event threshold is a different threshold than the motion alarm threshold.

21. The method of claim 7, wherein an increase step value of the motion alert level signal is greater than a decrease step value of the motion level signal.

22. A computer program product for monitoring a patient, comprising:
- a non-transitory computer-readable medium comprising:
  - code for causing a computer to receive a substantially live sequence of images of a patient location;
  - code for causing the computer to compare each image of the sequence of images with one or more preceding images to determine a sequence of motion levels associated with the sequence of images, each motion level of the sequence of motion levels representing an amount of change for at least one region of the each image relative to the at least one region of the one or more preceding images;
  - code for causing the computer to compare the sequence of motion levels associated with the sequence of images to a motion threshold;
  - code for causing the computer to determine a motion alert level signal based on the comparison by increasing the motion alert level signal responsive to determining that a first one or more motion levels of the sequence of motion levels exceeds the motion threshold and decreasing the motion alert level signal responsive to determining that a second one or more motion levels of the sequence of motion levels is less than the motion threshold;
  - code for causing the computer to compare the motion alert level signal with a motion alarm threshold; and
  - code for causing the computer to generate a motion alarm signal responsive to detecting that the motion level signal exceeds the motion alarm threshold.

23. The computer program product of claim 22, wherein the non-transitory computer-readable medium further comprises:
- code for causing the computer to trigger, responsive to the motion alarm signal, an audible alarm at a monitoring device; and
- code for causing the computer to enable, concurrently with the audible alarm, a substantially live display of the sequence of images on a display device of the monitoring device.

24. The computer program product of claim 22, further comprising:
- code for causing the computer to compare a first region of each image of the sequence of images with the first region of the one or more preceding images to generate a first motion level associated with the first region for each of the sequence of images;
- code for causing the computer to compare the first motion level to a first threshold to generate a first motion detection signal associated with the first region;
- code for causing the computer to compare a second region of each image of the sequence of images with the second region of the one or more preceding images to generate a second motion level associated with the second region for each of the sequence of images; and
- code for causing the computer to compare the second motion level to the first threshold to produce a second motion detection signal associated with the second region.

25. The computer program product of claim 24, further comprising:
- code for causing the computer to apply a first weighting coefficient to the first motion detection signal;
- code for causing the computer to apply a second weighting coefficient to the second motion detection signal; and
- code for causing the computer to determine the motion alert level signal based at least in part on the weighted first motion detection signal and the weighted second motion detection signal.

26. The computer program product of claim 22, further comprising:
- code for causing the computer to compare the motion alert level signal with a motion event threshold; and
- code for causing the computer to store, responsive to the motion alert level signal exceeding the motion event threshold, a time period of the sequence of images.

\* \* \* \* \*